United States Patent [19]

Ellestad et al.

[11] Patent Number: 5,053,394
[45] Date of Patent: Oct. 1, 1991

[54] TARGETED FORMS OF METHYLTRITHIO ANTITUMOR AGENTS

[75] Inventors: George A. Ellestad, Pearl River, N.Y.; William J. McGahren, Demarest, N.J.; Martin L. Sassiver, Spring Valley, N.Y.; Philip R. Hamann, Garnerville, N.Y.; Lois M. Hinman, Tarrytown, N.Y.; Janis Upeslacis, Pomona, N.Y.

[73] Assignee: American Cyanamid Company, Stamford, Conn.

[21] Appl. No.: 339,343

[22] Filed: Apr. 14, 1989

Related U.S. Application Data

[63] Continuation-in-part of Ser. No. 246,248, Sep. 21, 1988, abandoned, which is a continuation-in-part of Ser. No. 114,940, Oct. 30, 1987, abandoned.

[51] Int. Cl.$^5$ ............ A01N 43/04; A01N 45/00; C12P 19/44; A61K 39/00
[52] U.S. Cl. .................... 514/25; 435/74; 514/26; 514/53; 424/85.91; 536/16.8; 536/17.5
[58] Field of Search ............ 514/5, 12, 25, 26; 424/85.91

[56] References Cited

U.S. PATENT DOCUMENTS 4,552,867 11/1985 Martin et al. ............ 514/18
4,970,198 11/1990 Lee et al. ............ 514/25

Primary Examiner—Frederick E. Waddell
Assistant Examiner—T. J. Criares
Attorney, Agent, or Firm—H. G. Jackson

[57] ABSTRACT

This disclosure describes a method for constructing carrier-drug conjugates from the family of methyltrithio antibacterial and antitumor agents.

33 Claims, 17 Drawing Sheets

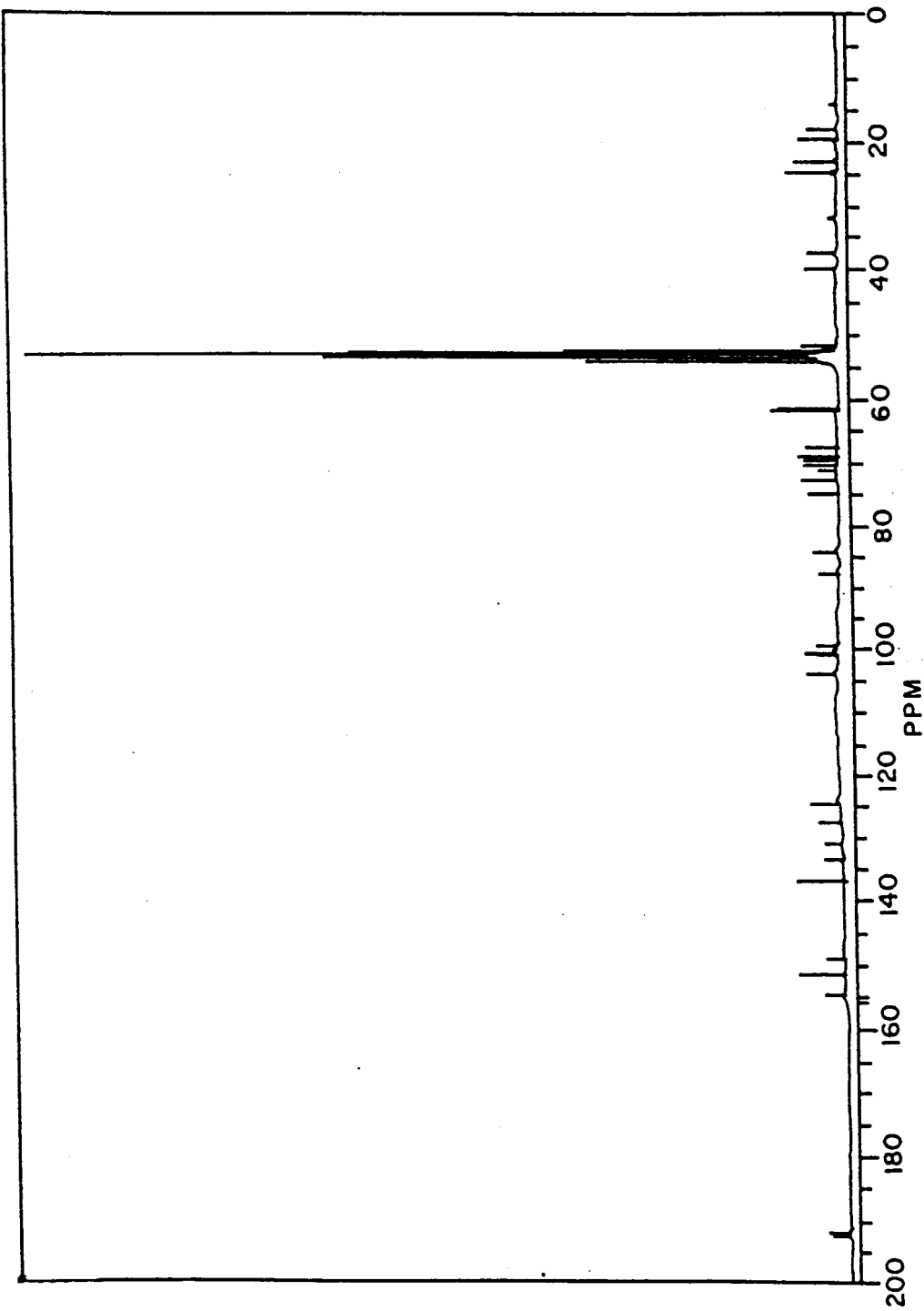

TARGETED FORMS OF METHYLTRITHIO ANTITUMOR AGENTS

This application is a continuation-in-part of copending application Ser. No. 246,248, filed Sept. 21, 1988 (now abandoned) which is a continuation-in-part of 07/114,940, filed Oct. 30, 1987 (now abandoned).

SUMMARY OF THE INVENTION

The invention describes carrier-drug conjugates of the disulfide analogs of the $\alpha_1$, $\alpha_2$, $\alpha_3$, $\alpha_4$, $\beta_1$, $\beta_2$, $\gamma_1$, $\delta_1$ and pseudoaglycone components of the LL-E33288 complex and derivatives thereof, as well as the disulfide analogs of BBM-1675, FR-900405, FR-900406, PD 114759, PD 115028, CL-1577A, CL-1577B, CL-1577D, CL-1577E and CL-1724 antitumor antibiotics and derivatives thereof. The carrier portion of the conjugate is a mono-or polyclonal antibody, their fragments, chemically or genetically manipulated counterparts, or growth factors or steroids. The invention includes the method of using the carrier-drug conjugates as well as their process of manufacture.

DESCRIPTION OF THE DRAWINGS

FIG. I: The ultraviolet spectrum of the antitumor antibiotic designated as LL-E33288$\gamma_1^I$.

FIG. II: The proton magnetic resonance spectrum of the antitumor antibiotic designated as LL-E33288$\gamma_1^I$.

Figure 1:
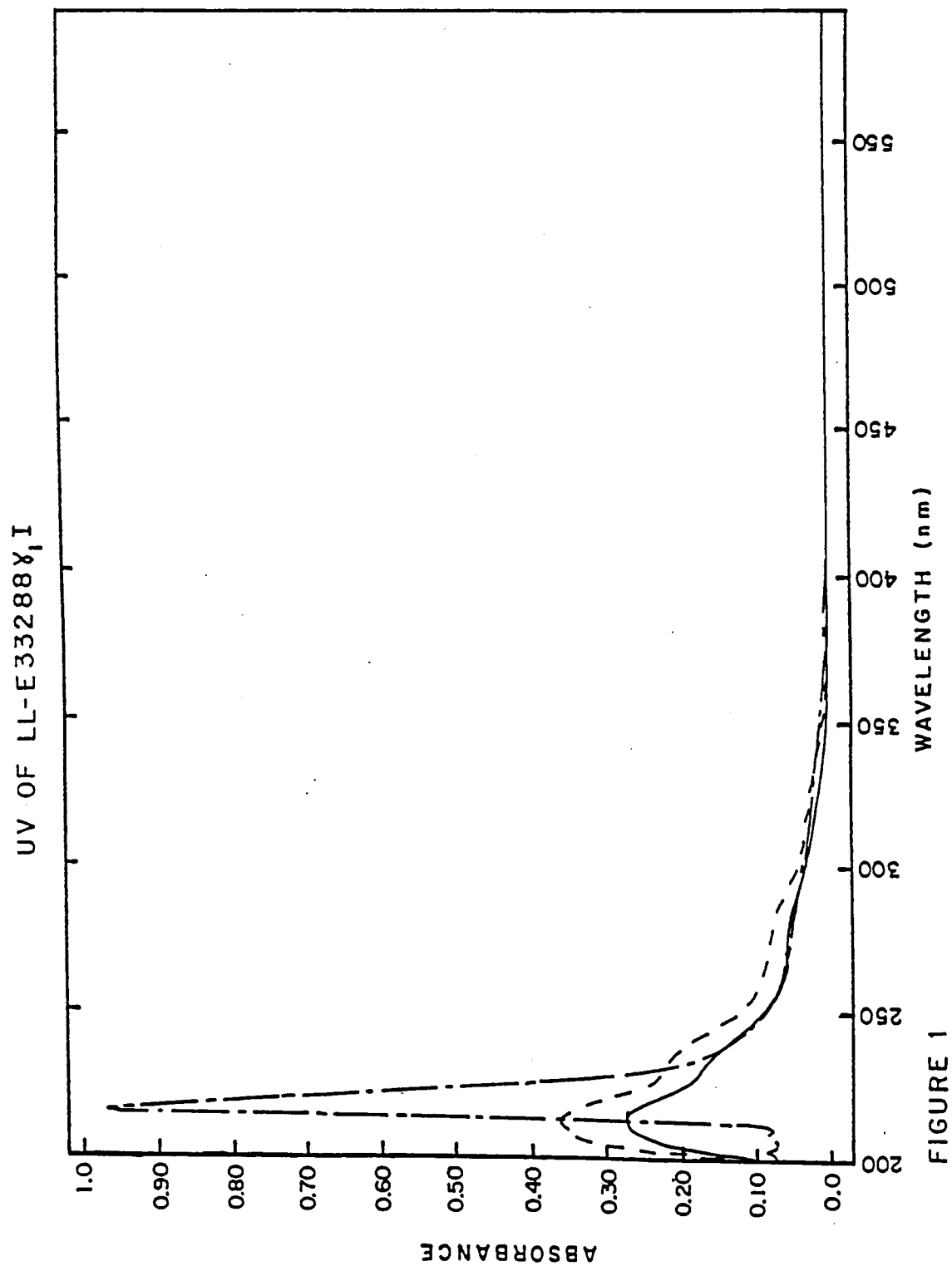
Figure 2:
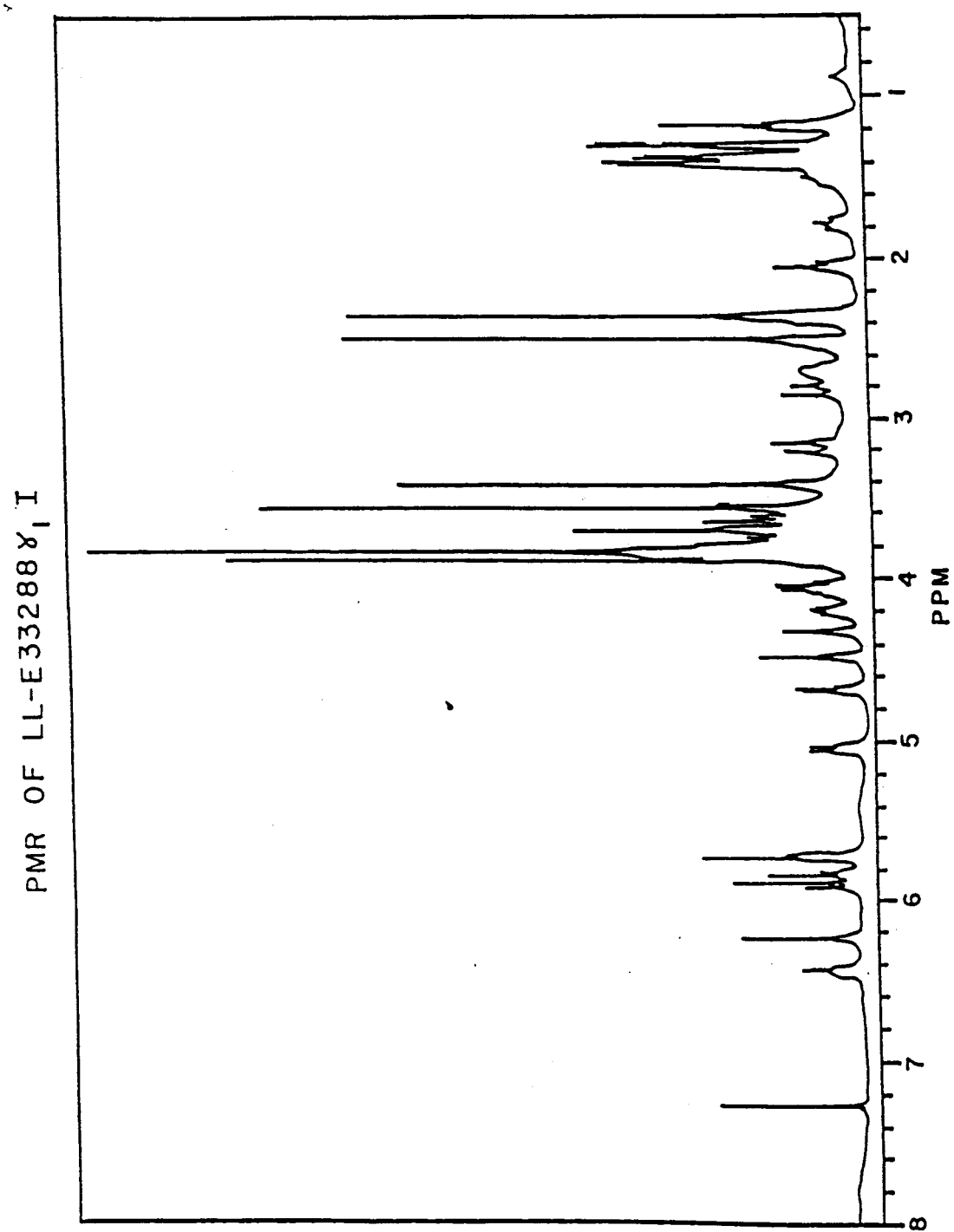
Figure 3:
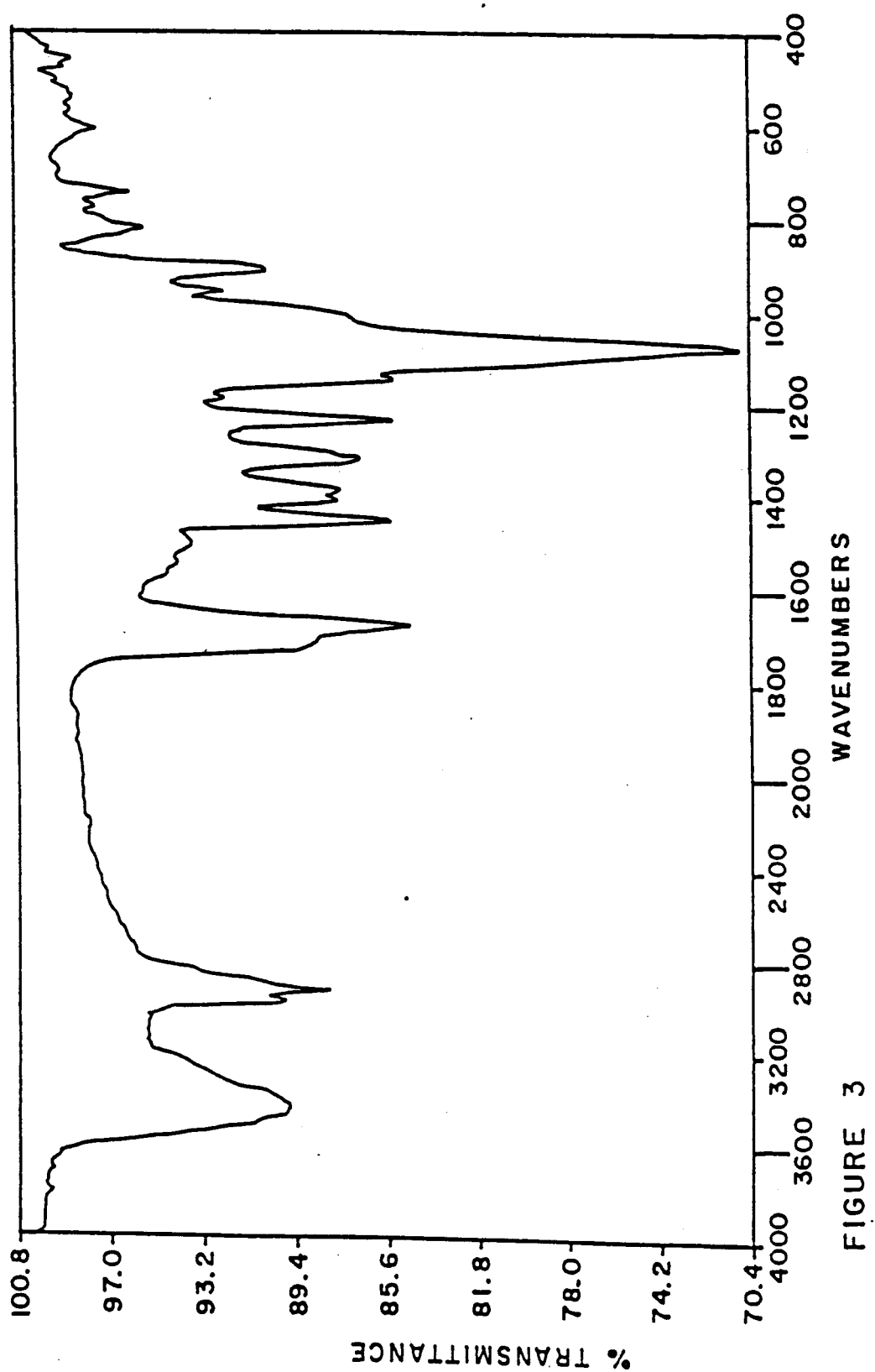
Figure 4:
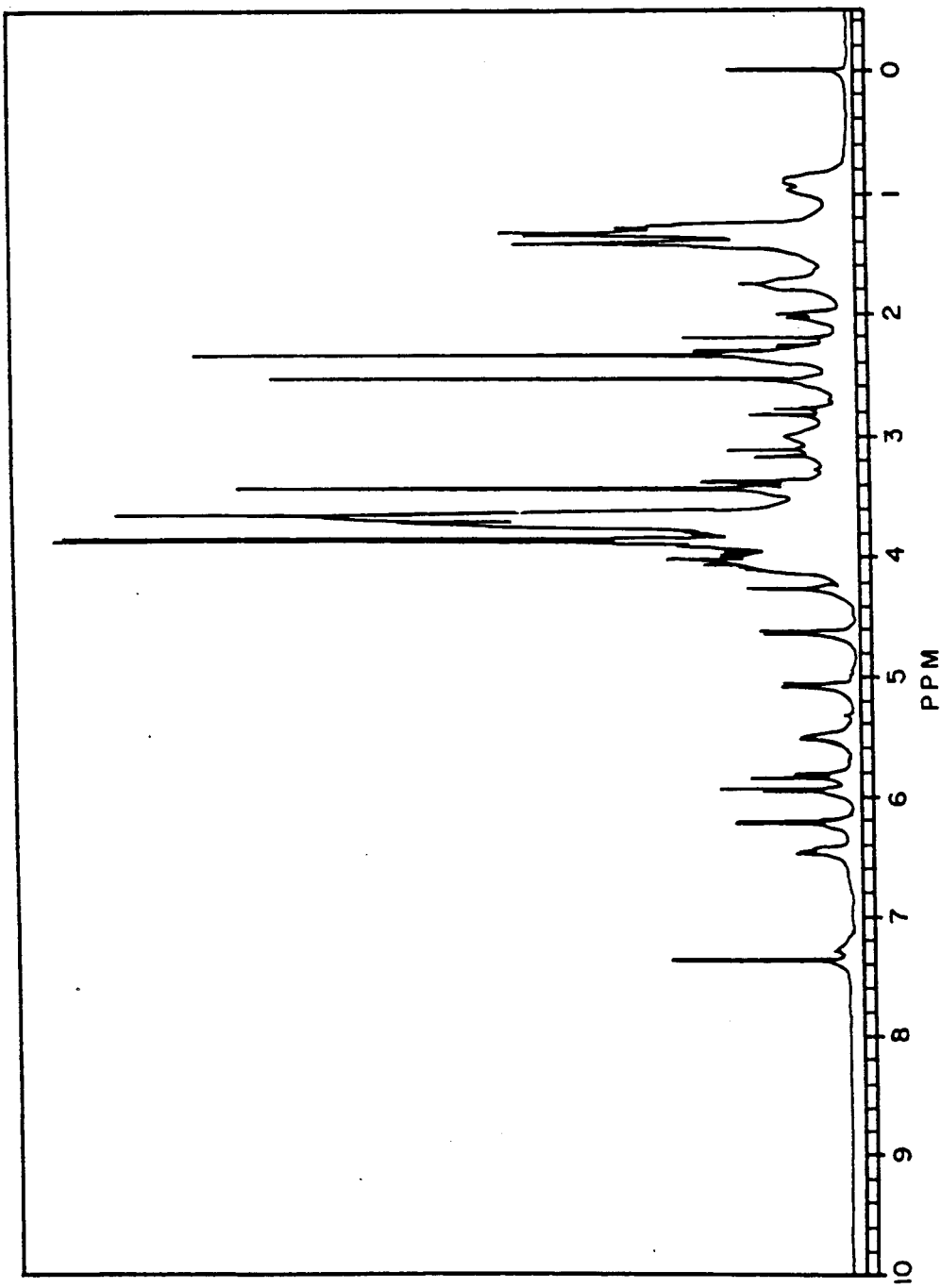
Figure 5:
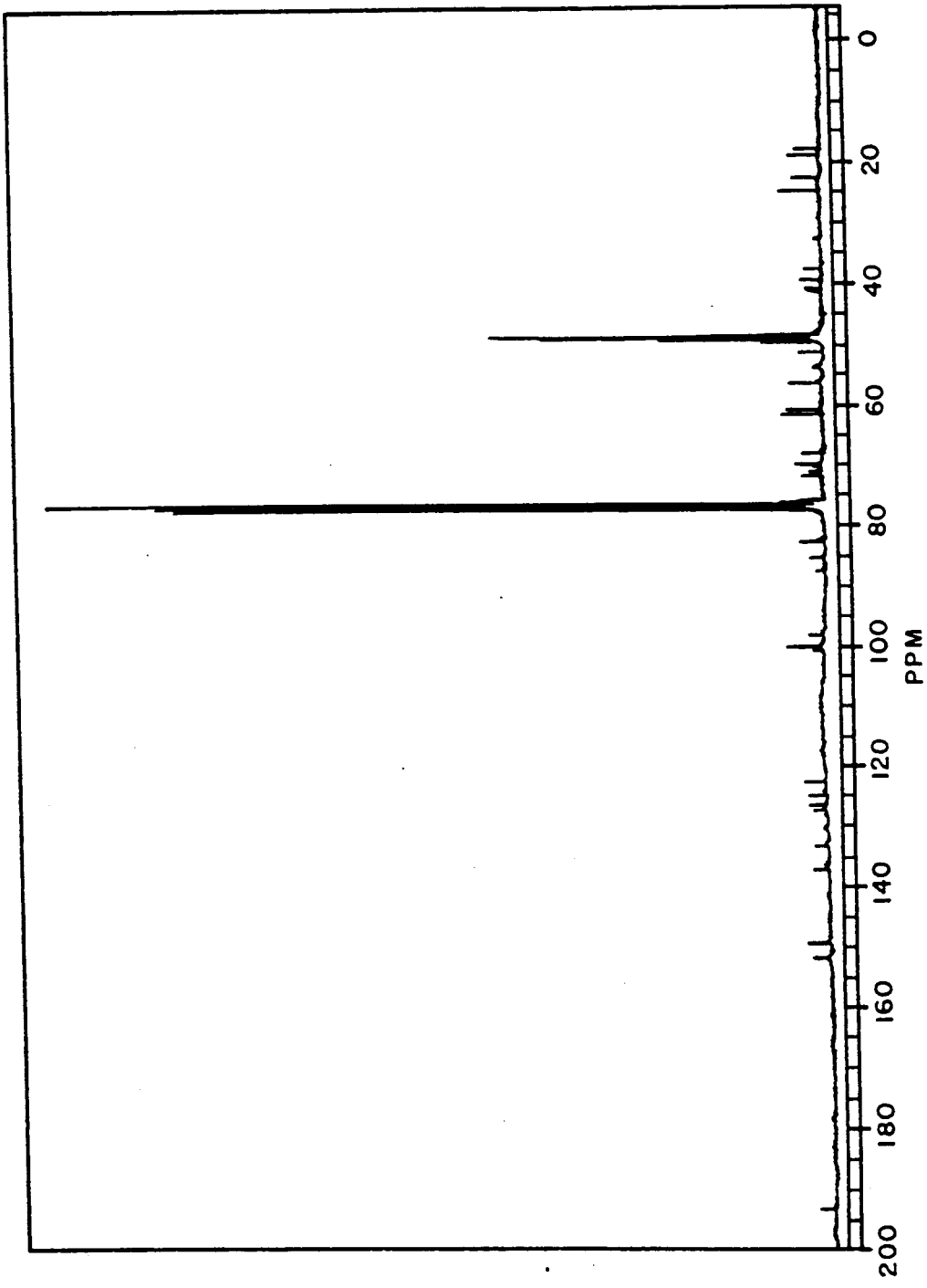
Figure 6:
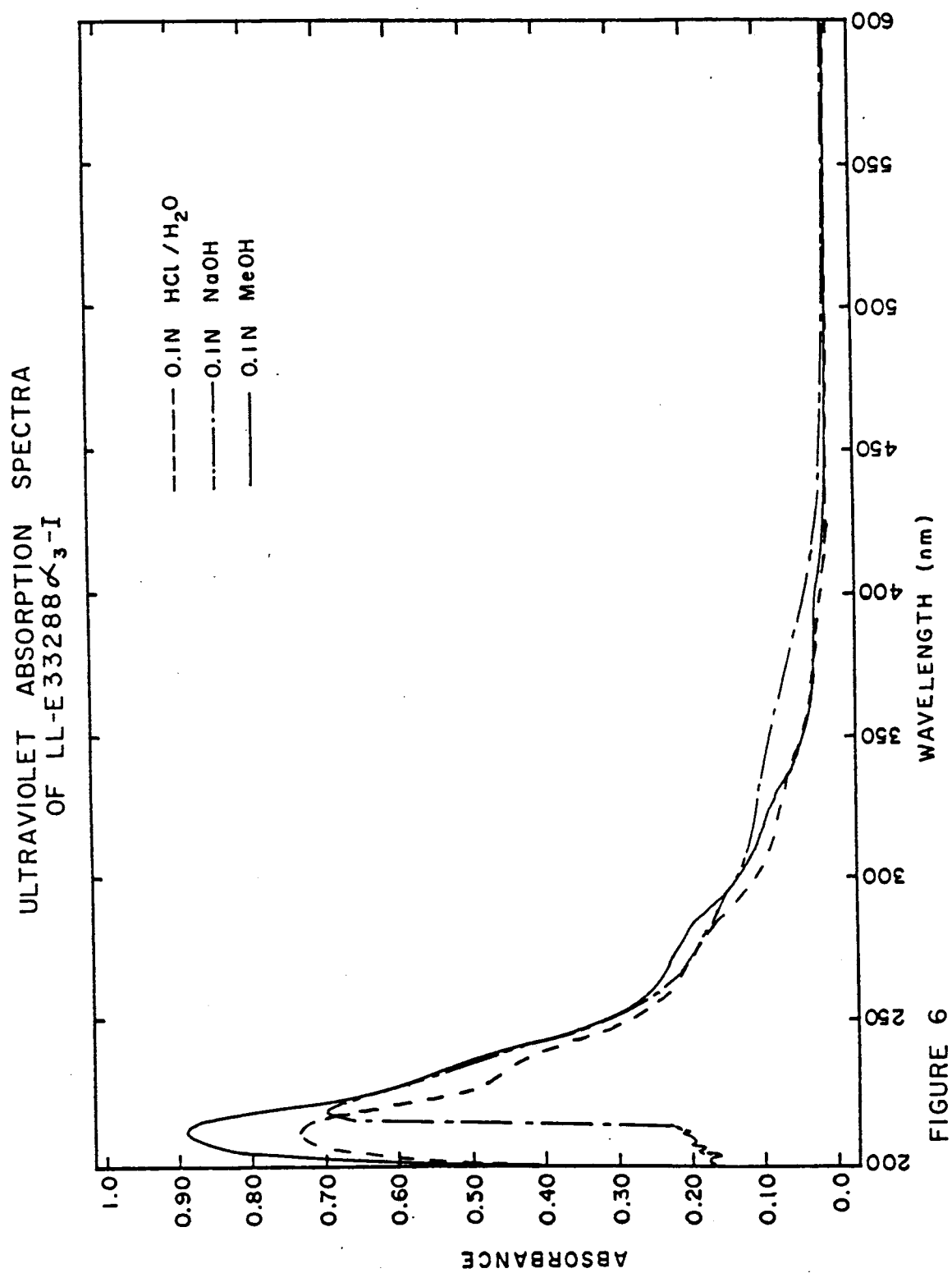
Figure 7:
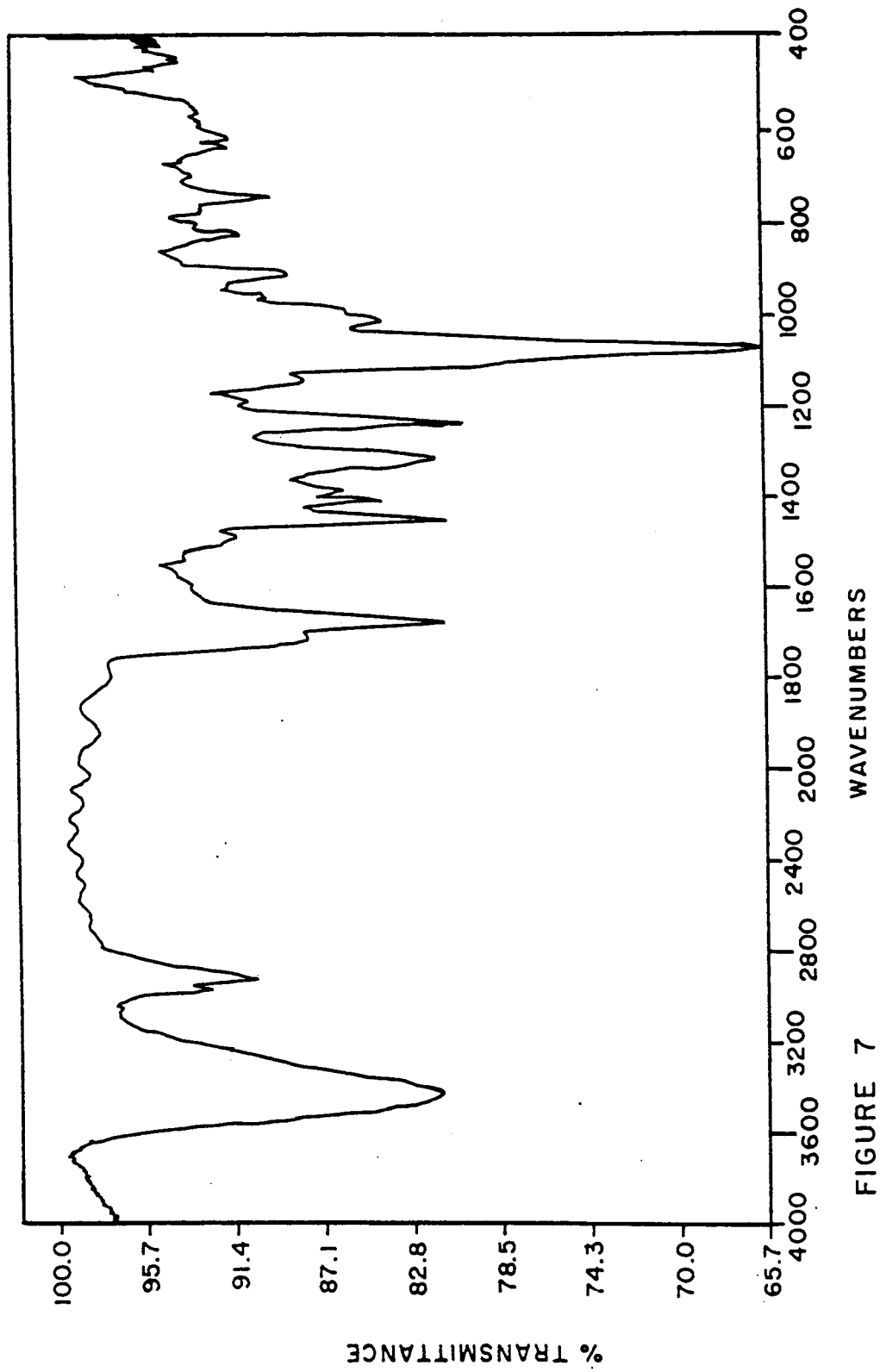
Figure 8:
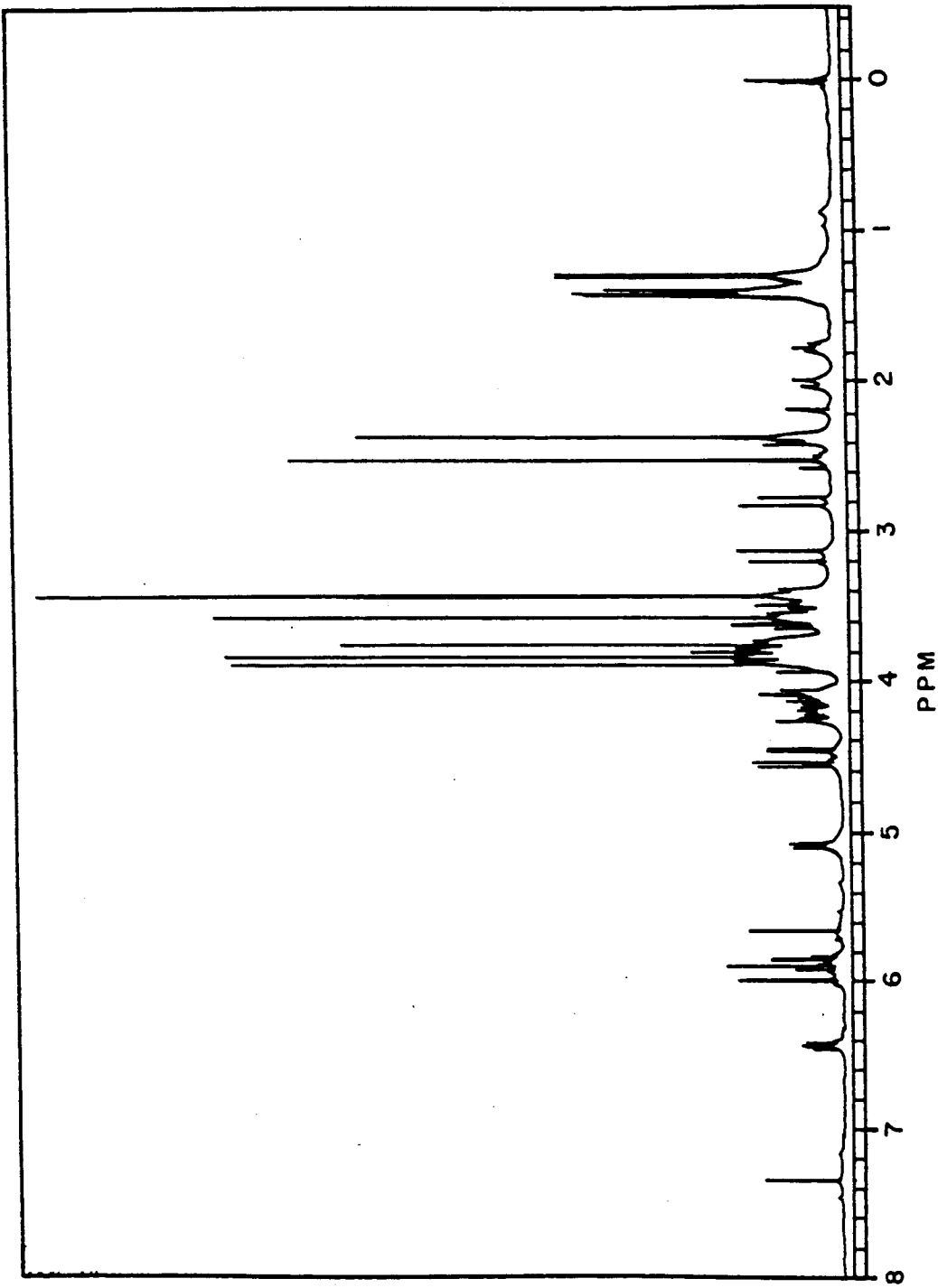
Figure 9:
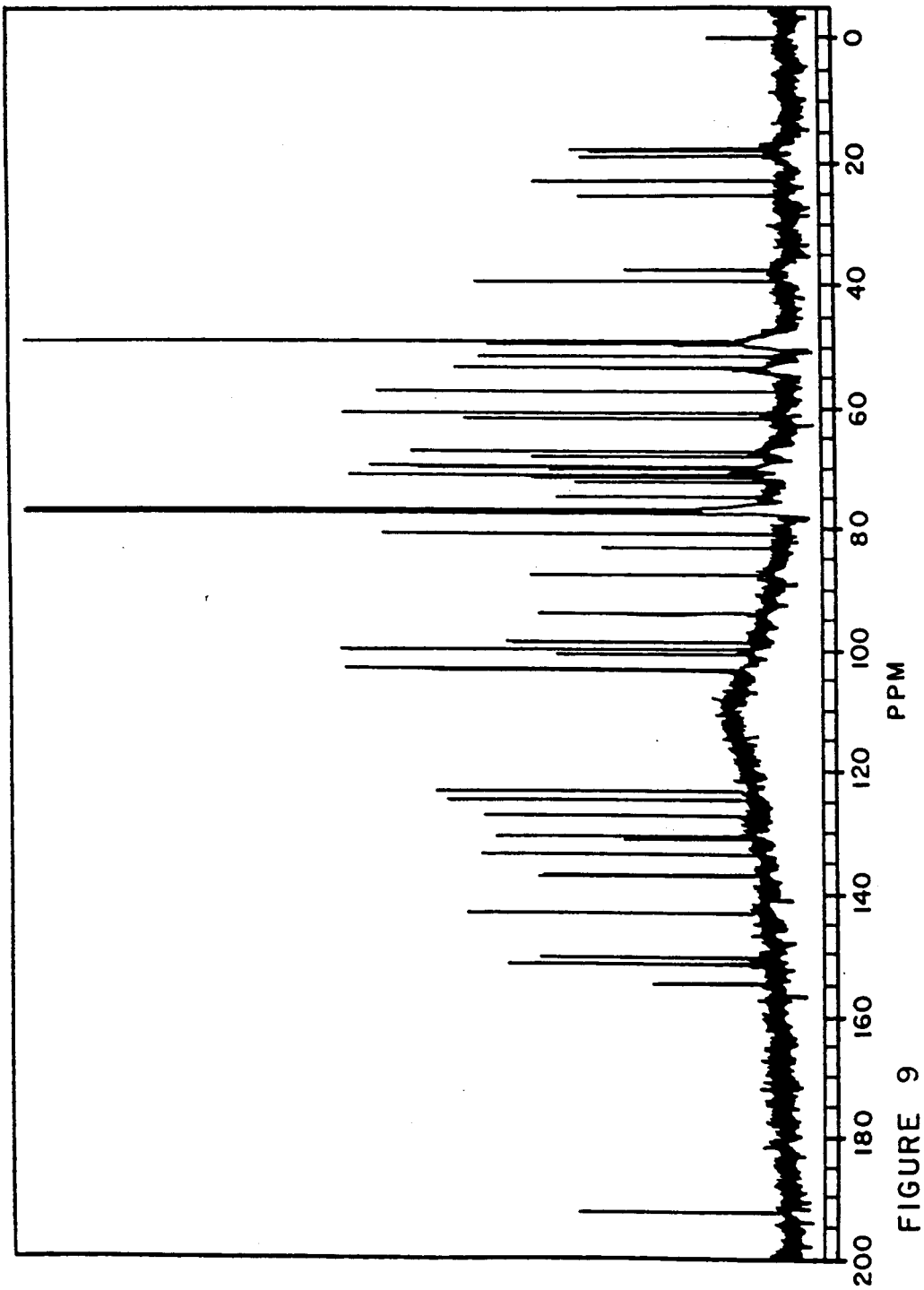
Figure 10:
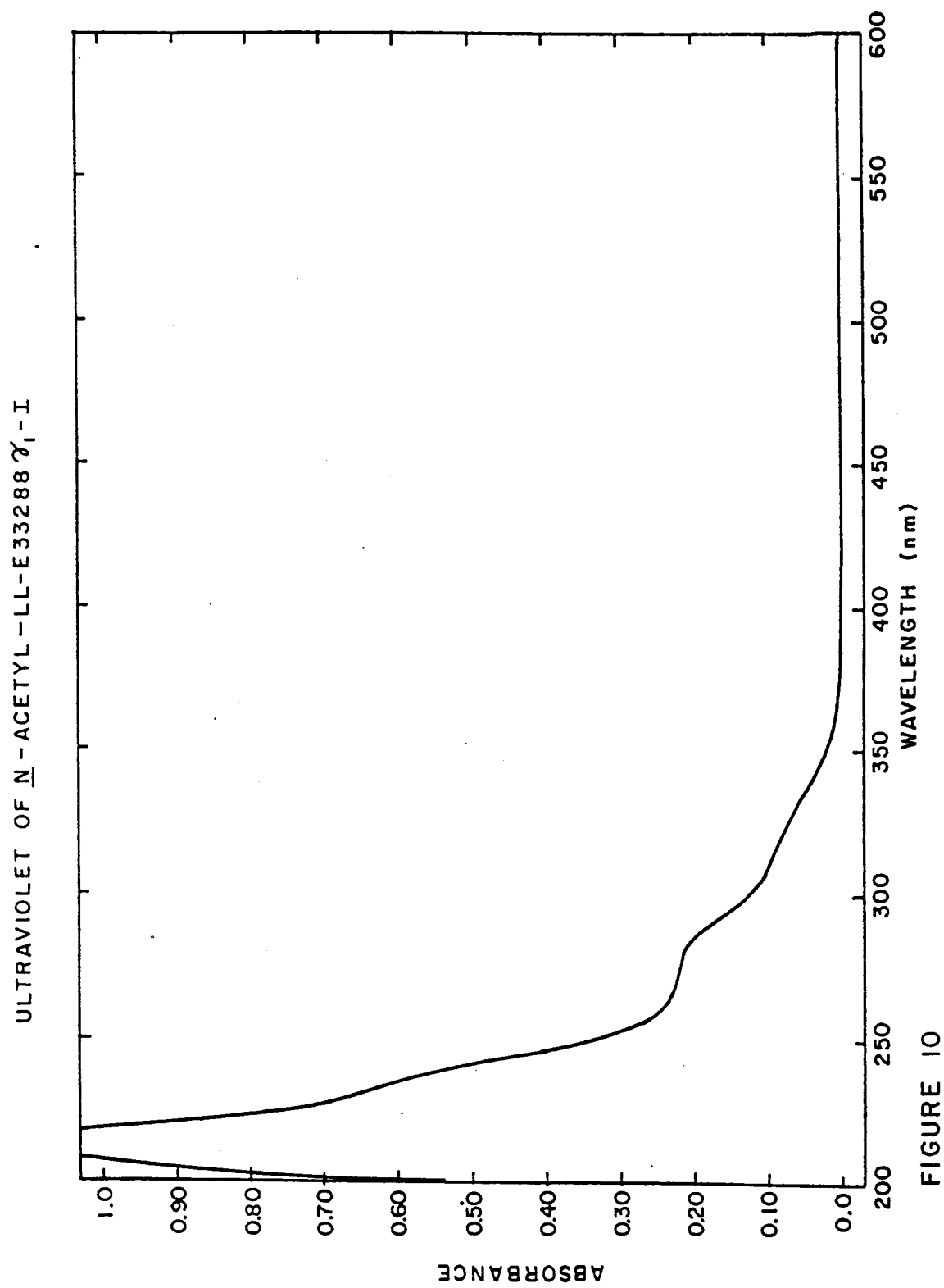
Figure 11:
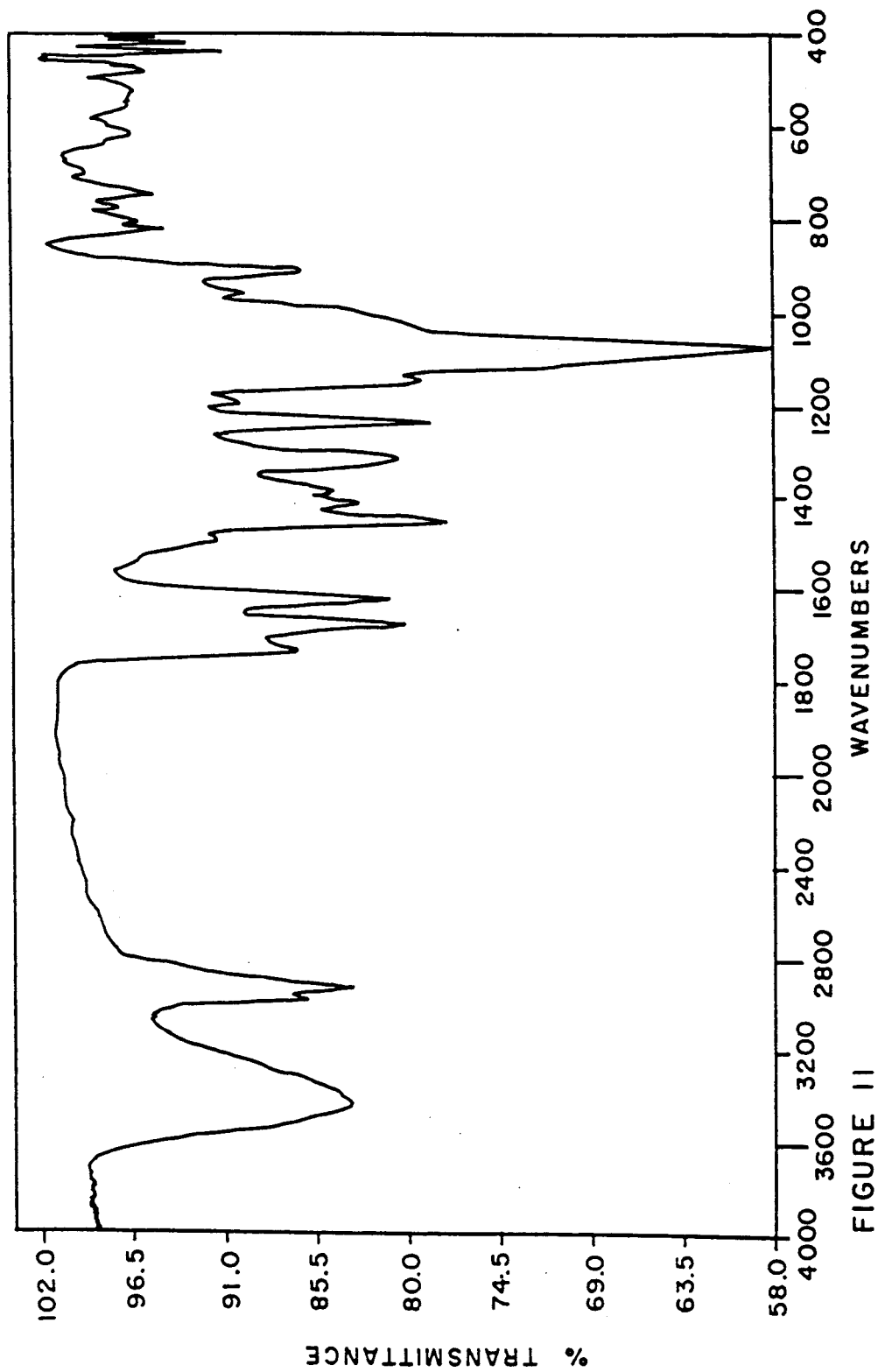
Figure 12:
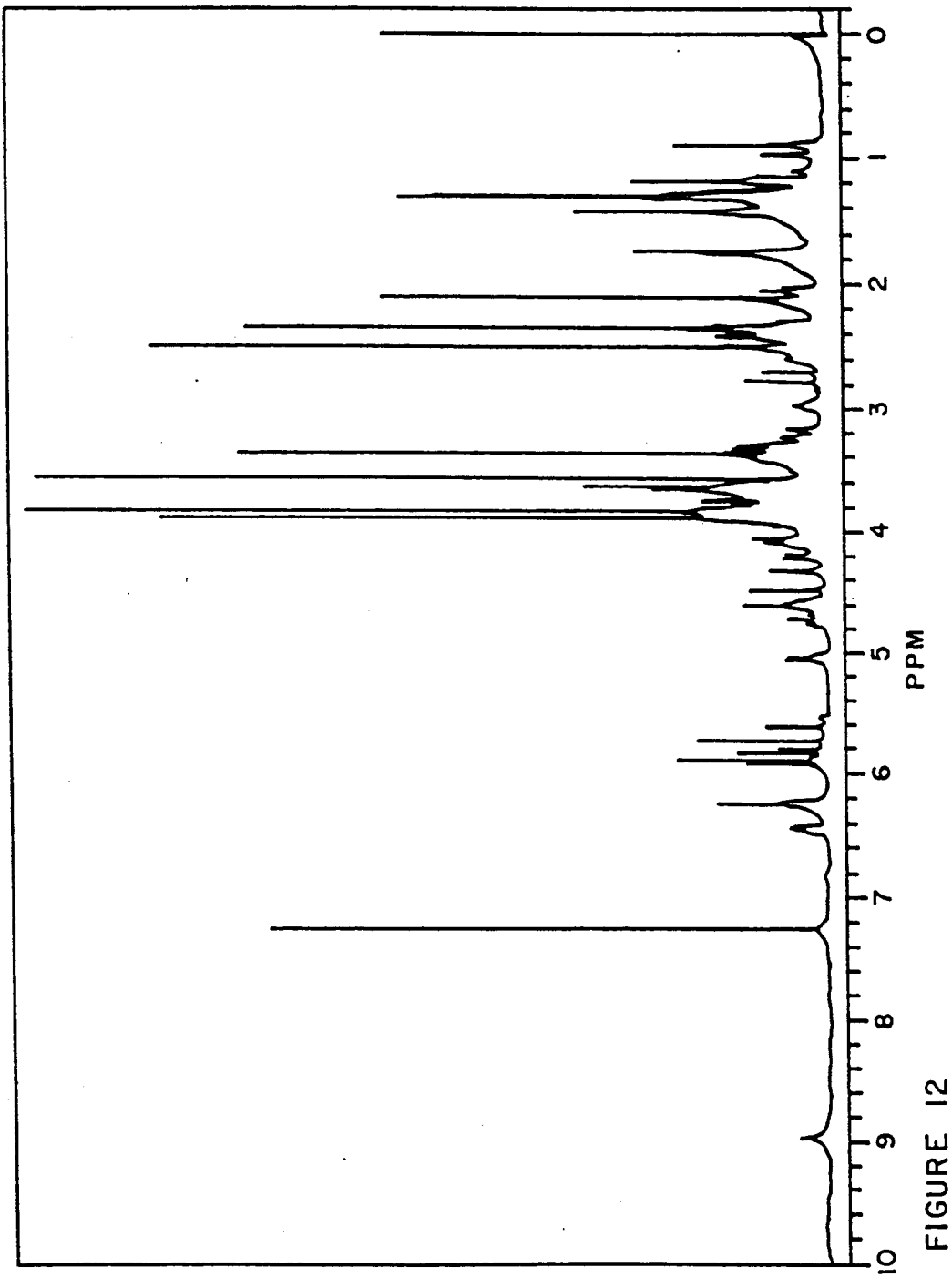
Figure 13:
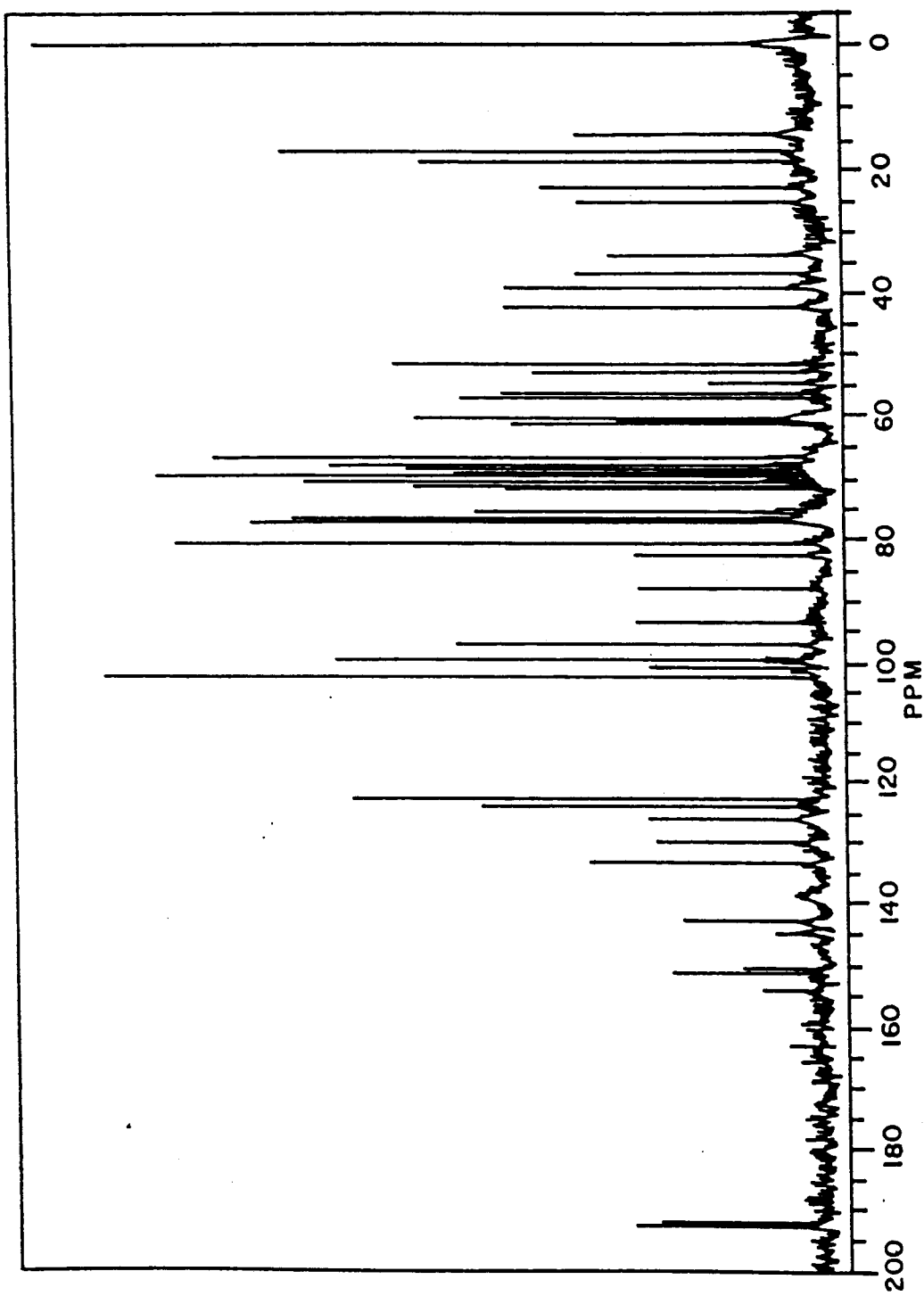
Figure 14:
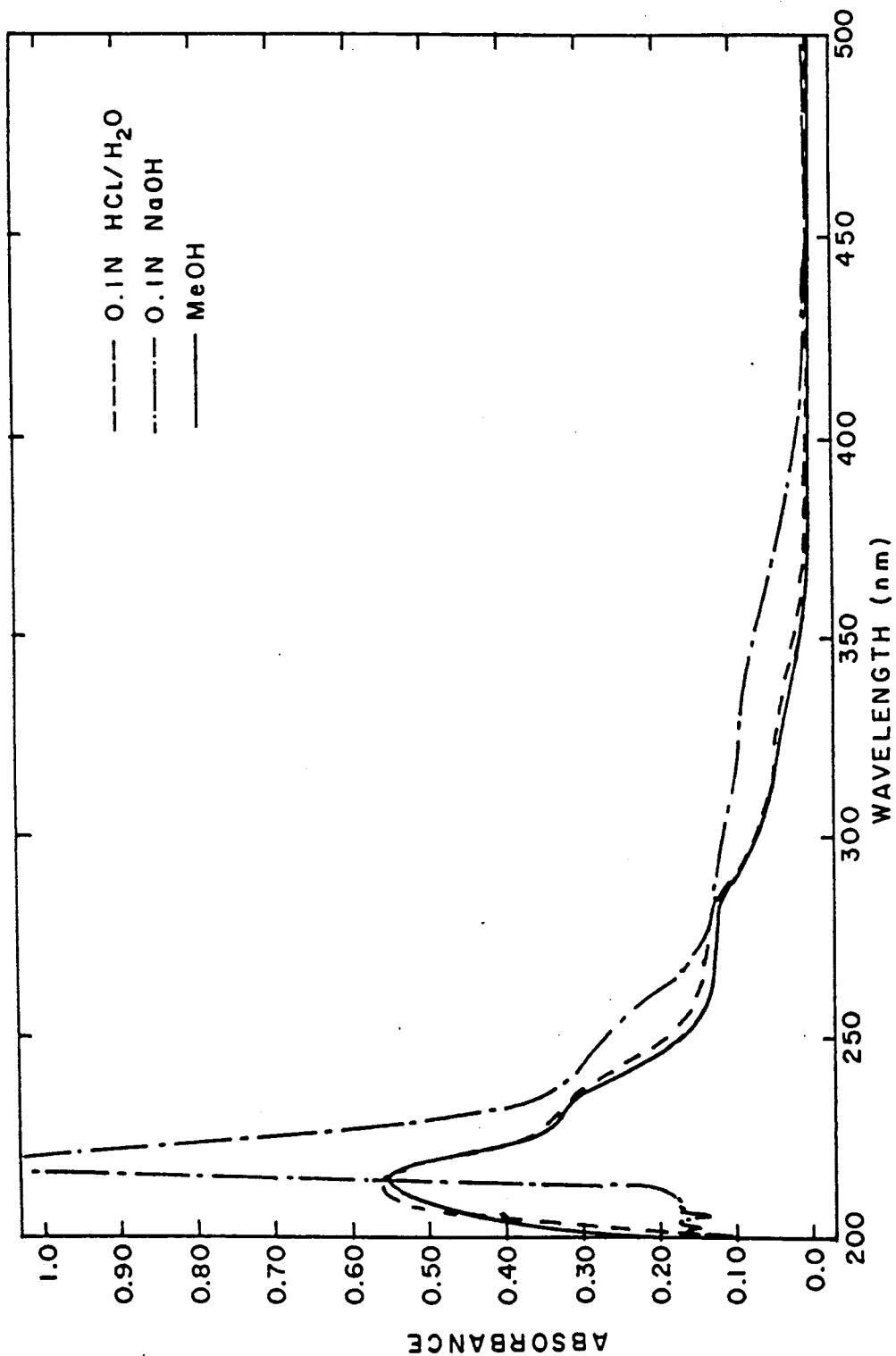
Figure 15:
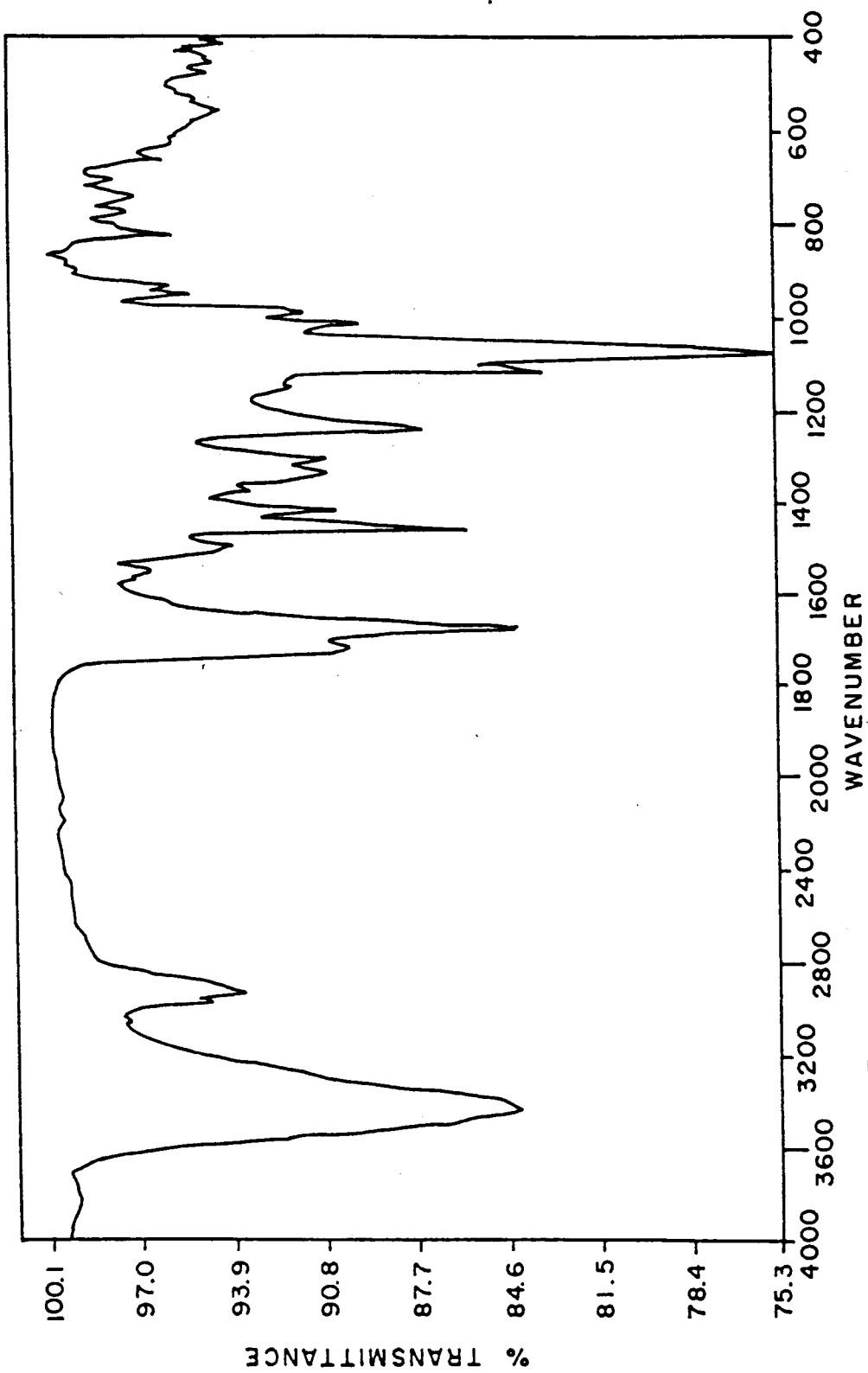
Figure 16:
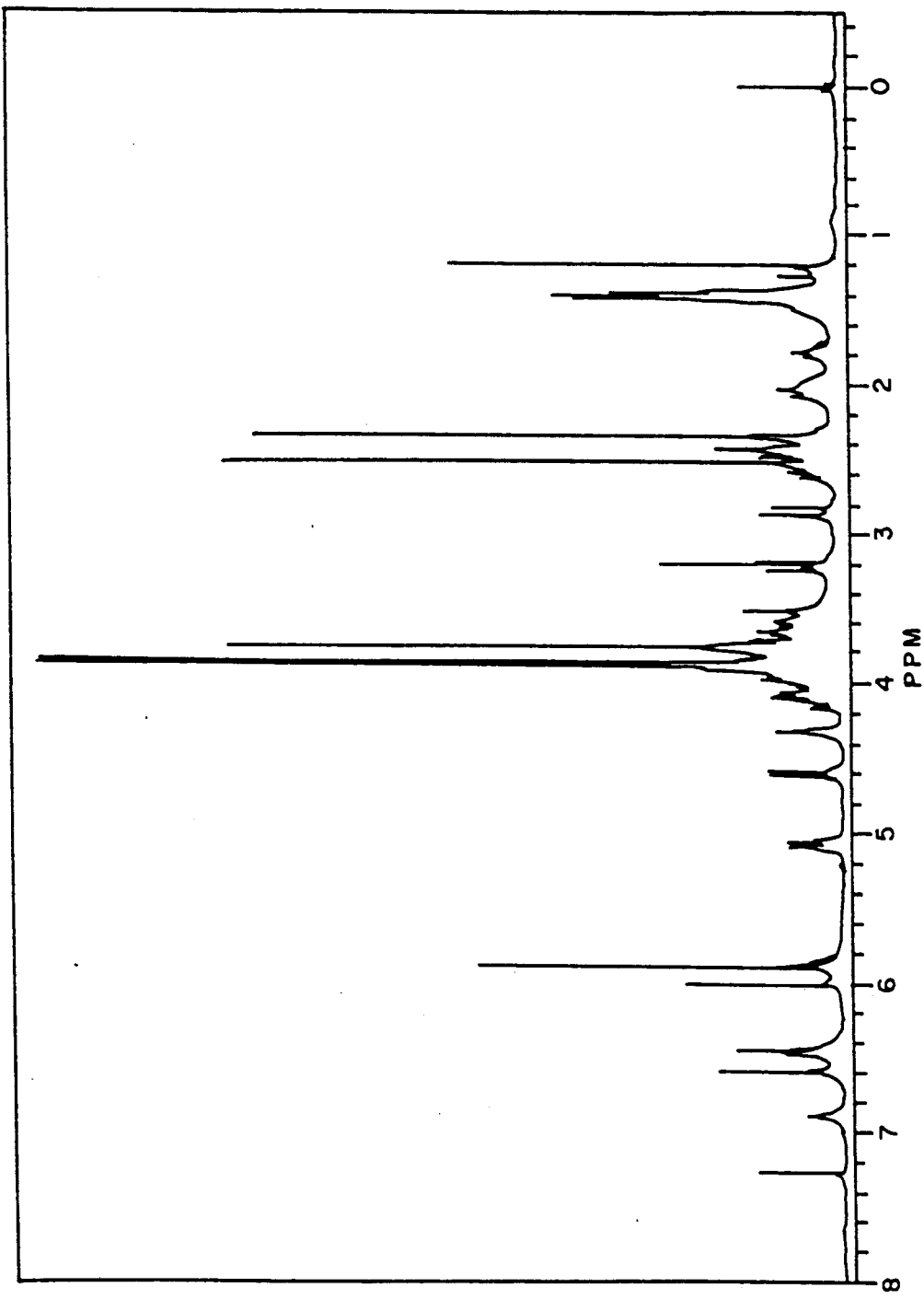

FIG. III: The infrared spectrum of the antitumor antibiotic designated as LL-E33288$\gamma_1^I$.

FIG. IV: The proton magnetic resonance spectrum of the antitumor antibiotic designated as LL-E33288$\alpha_2^I$.

FIG. V: The carbon-13 nuclear magnetic resonance spectrum of the antitumor antibiotic designated as LL-E33288$\alpha_2^I$.

FIG. VI: The ultraviolet spectrum of the antitumor antibiotic designated ass LL-E33288$\alpha_3^I$.

FIG. VII: The infrared spectrum of the antitumor antibiotic designated as LL-E33288$\alpha_3^I$.

FIG. VIII: The proton magnetic resonance spectrum of the antitumor antibiotic designated as LL-E33288$\alpha_3^I$.

FIG. IX: The carbon-13 nuclear magnetic resonance spectrum of the antitumor antibiotic designated as LL-E33288$\alpha_3^I$.

FIG. X: The ultraviolet spectrum of the antitumor antibiotic designated as N-acetyl LL-E33288$\delta_1^I$.

FIG. XI: The infrared spectrum of the antitumor antibiotic designated as N-acetyl LL-E33288$\delta_1^I$.

FIG. XII: The proton magnetic resonance spectrum of the antitumor antibiotic designated as N-acetyl LL-E33288$\delta_1^I$.

FIG. XIII: The carbon-13 nuclear magnetic resonance spectrum of the antitumor antibiotic designated as N-acetyl LL-E33288$\delta_1^I$.

FIG. XIV: The ultraviolet spectrum of the antitumor antibiotic designated as iodo LL-E33288 pseudoaglycone.

FIG. XV: The infrared spectrum of the antitumor antibiotic designated as iodo LL-E33288 pseudoaglycone.

FIG. XVI: The proton magnetic resonance spectrum of the antitumor antibiotic designated as iodo LL-E33288 pseudoaglycone.

FIG. XVII: The carbon-13 magnetic resonance spectrum of the antitumor antibiotic designated as iodo LL-E33288 pseudoaglycone.

DETAILED DESCRIPTION OF THE INVENTION

The family of antibacterial and antitumor agents, known collectively as the LL-E33288 complex are described and claimed in U.S. Pat. No. 4,970,198 (1990) and are used to prepare the disulfur antitumor agents which are some of the starting materials for targeted forms of the antitumor agents of our invention.

The Ser. No. 009,321 application describes the LL-E33288 complex, the components thereof, namely, LL-E33288$\alpha_1^{Br}$, LL-E33288$\alpha_1^I$, LL-E33288$\alpha_2^{Br}$, LL-E33288$\alpha_2^I$, LL-E33288$\alpha_3^{Br}$, LL-E33288$\alpha_3^I$, LL-E33288$\alpha_4^{Br}$, LL-E33288$\beta_1^{Br}$, LL-E33288$\beta_1^I$, LL-E33288$\beta_2^{Br}$, LL-E33288$\beta_2^I$, LL-E33288$\delta_1^{Br}$, LL-E33288$\delta_1^I$ and LL-E33288$\delta_1^I$, and methods for their production by aerobic fermentation utilizing a new strain of *Micromonospora echinospora* ssp *calichensis* or natural or derived mutants thereof. Ser. No. 009,321 also discloses proposed structures for some of the above named components. These proposed structures are reproduced in Table 1.

TABLE 1

Proposed Structures for $CH_3$—SSS—W isolated from natural sources (wherein W is the substituent attached to $CH_3$—SSS— below)

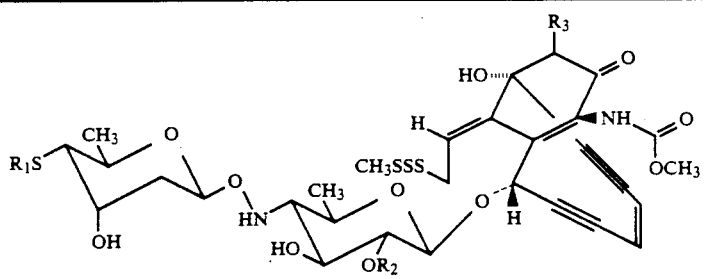

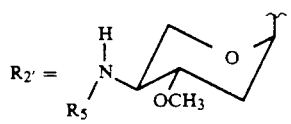

TABLE 1-continued

Proposed Structures for $CH_3$—SSS—W isolated from natural sources (wherein W is the substituent attached to $CH_3$—SSS— below)

$R_{3'}=$ 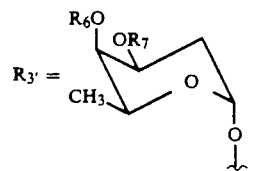

$R_{4'}=$ 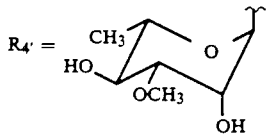

$Ar_1=$ 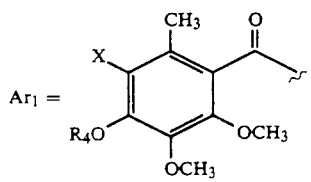

$Ar_2=$ 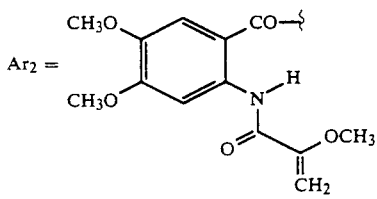

| Designation | $R_1$ | $R_2$ | $R_3$ | $R_4$ | $R_5$ | $R_6$ | $R_7$ | X |
|---|---|---|---|---|---|---|---|---|
| $E33288\alpha_2^I$ | $Ar_1$ | $R_{2'}$ | H | H | $C_2H_5$ | | | I |
| $E33288\alpha_3^I$ | $Ar_1$ | H | H | $R_{4'}$ | | | | I |
| $E33288\beta_1^I$ | $Ar_1$ | $R_{2'}$ | H | $R_{4'}$ | $(CH_3)_2CH$ | | | I |
| $E33288\gamma_1^I$ | $Ar_1$ | $R_{2'}$ | H | $R_{4'}$ | $C_2H_5$ | | | I |
| $E33288\delta_1^I$ | $Ar_1$ | $R_{2'}$ | H | $R_{4'}$ | $CH_3$ | | | I |
| $E33288\beta_1^{Br}$ | $Ar_1$ | $R_{2'}$ | H | $R_{4'}$ | $(CH_3)_2CH$ | | | Br |
| $E33288\gamma_1^{Br}$ | $Ar_1$ | $R_{2'}$ | H | $R_{4'}$ | $C_2H_5$ | | | Br |
| $E33288\alpha_2^{Br}$ | $Ar_1$ | $R_{2'}$ | H | H | $C_2H_5$ | | | Br |
| $E33288\alpha_3^{Br}$ | $Ar_1$ | H | H | $R_{4'}$ | | | | Br |
| Esperamicin $A_1$ | $CH_3$ | $R_{2'}$ | $R_{3'}$ | | $(CH_3)_2CH$ | H | $Ar_2$ | |
| Esperamicin $A_2$ | $CH_3$ | $R_{2'}$ | $R_{3'}$ | | $(CH_3)_2CH$ | $Ar_2$ | H | |
| Esperamicin $A_{1b}$ | $CH_3$ | $R_{2'}$ | $R_{3'}$ | | $CH_3CH_2$ | H | $Ar_2$ | |

Additional members of the LL-E33288 complex are described and claimed in U.S. Pat. No. 4,939,244 (1990) and are likewise useful for preparing the targeted forms of the antitumor agents of our invention. This application describes the LL-E33288bromo- and iodo-pseudoaglycones of the series, which have been prepared by chemical means. The application also describes dihydro derivatives accessable from all the above-named antitumor antibiotics through sodium borohydride reduction of the ketone at $C_{11}$ to a hydroxyl group. These latter proposed structures are reproduced in Table 2.

Still other members of the LL-E33288 family of antitumor antibiotics are described and claimed in our copending U.S. patent application Ser. No. 338,928, filed on Apr. 14, 1989, and also are useful for preparing additional targeted forms of the antitumor agents of our invention. This application describes N-acyl derivatives of several members of the LL-E33288 complex which have been prepared by chemical means. These proposed structures are likewise reproduced in Table 2.

TABLE 2

Proposed Structures for CH₃—SSS—W derived from chemical manipulation of the compounds of Table 1 (wherein W is the substituent attached to CH₃—SSS— below)

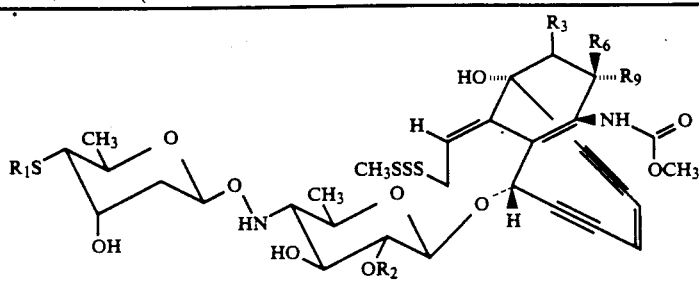

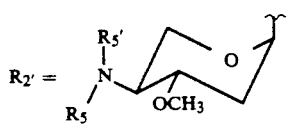

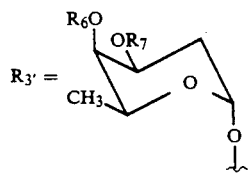

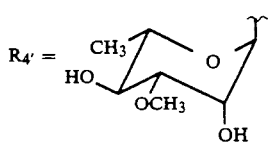

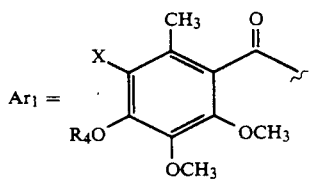

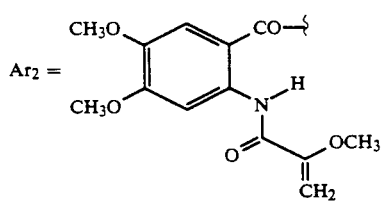

| Designation | R₁ | R₂ | R₃ | R₄ | R₅ | R₅' | R₆ | R₇ | R₈ | R₉ | X |
|---|---|---|---|---|---|---|---|---|---|---|---|
| Dihydro LL-E33288α₂¹ | Ar₁ | R₂' | H | H | C₂H₅ | H | | | OH | H | I |
| N-Acyl LL-E33288α₂¹ | Ar₁ | R₂' | H | H | C₂H₅ | RCO | | | =O | | I |
| Dihydro LL-E33288α₃¹ | Ar₁ | H | H | R₄' | | | | | OH | H | I |
| Dihydro LL-E33288β₁¹ | Ar₁ | R₂' | H | R₄' | (CH₃)₂CH | H | | | OH | H | I |
| N-Acyl LL-E33288β₁¹ | Ar₁ | R₂' | H | R₄' | (CH₃)₂CH | RCO | | | =O | | I |
| Dihydro LL-E33288γ₁¹ | Ar₁ | R₂' | H | R₄' | C₂H₅ | H | | | OH | H | I |
| N-Acyl LL-E33288γ₁¹ | Ar₁ | R₂' | H | R₄' | C₂H₅ | RCO | | | =O | | I |
| Dihydro LL-E33288δ₁¹ | Ar₁ | R₂' | H | R₄' | CH₃ | H | | | OH | H | I |
| N-Acyl LL-E33288δ₁¹ | Ar₁ | R₂' | H | R₄' | CH₃ | RCO | | | =O | | I |
| Iodo LL-E33288 pseudoaglycone | Ar₁ | H | H | H | | | | | =O | | I |
| Dihydro-iodo LL-E33288 pseudoaglycone | Ar₁ | H | H | H | | | | | OH | H | I |
| Dihydro LL-E33288β₁^Br | Ar₁ | R₂' | H | R₄' | (CH₃)₂CH | H | | | OH | H | Br |
| N-Acyl LL-E33288β₁^Br | Ar₁ | R₂' | H | R₄' | (CH₃)₂CH | RCO | | | =O | | Br |
| Dihydro LL-E33288γ₁^Br | Ar₁ | R₂' | H | R₄' | C₂H₅ | H | | | OH | H | Br |
| N-Acyl LL-E33288γ₁^Br | Ar₁ | R₂' | H | R₄' | C₂H₅ | RCO | | | =O | | Br |
| Dihydro LL-E33288α₂^Br | Ar₁ | R₂' | H | H | C₂H₅ | H | | | OH | H | Br |
| N-Acyl LL-E33288α₂^Br | Ar₁ | R₂' | H | H | C₂H₅ | RCO | | | =O | | Br |
| Dihydro-E33288α₃^Br | Ar₁ | H | H | R₄' | | | | | OH | H | Br |
| Bromo LL-E33288 pseudoaglycone | Ar₁ | H | H | H | | | | | =O | | Br |

TABLE 2-continued
Proposed Structures for CH₃—SSS—W derived from chemical manipulation of the compounds of Table I (wherein W is the substituent attached to CH₃—SSS— below)

| | | | | | | | | | | |
|---|---|---|---|---|---|---|---|---|---|---|
| Dihydro-bromo LL-E33288 pseudoaglycone | Ar₁ | H | H | H | | | | OH | H | Br |
| N-Acetyl Esperamicin A₁ | CH₃ | R₂' | R₃' | | (CH₃)₂CH | CH₃CO | H | | | Ar₂ |
| N-Acetyl Esperamicin A₂ | CH₃ | R₂' | R₃' | | (CH₃)₂CH | CH₃CO | Ar₂ | | H | |
| N-Acetyl Esperamicin A₁ᵦ | CH₃ | R₂' | R₃' | | CH₃CH₂ | CH₃CO | H | | | Ar₂ |

R = hydrogen or a branched or unbranched alkyl ($C_1-C_{10}$) or alkylene ($C_1-C_{10}$) group, an aryl or heteroaryl group, or an aryl-alkyl ($C_1-C_5$) or heteroaryl-alkyl ($C_1-C_5$) group, all optionally substituted by one or more hydroxy, amino, carboxy, halo, nitro lower ($C_1-C_3$) alkoxy, or lower ($C_1-C_5$) thioalkoxy groups.

Certain other antibiotics are useful in our invention, namely:

1) Esperamicin BBM-1675, a novel class of potent antitumor antibiotics. I. Physico-chemical data and partial structure. M. Konishi, et. al., J. Antibiotics, 38, 1605 (1985). A new antitumor antibiotic complex, M. Konishi, et. al., U.K. Patent Application BG 2,141,425A, May 15, 1984 and U.S. Pat. No. 4,675,187 (1987).
2) New antitumor antibiotics, FR-900405 and FR-900406.I. Taxonomy of the producing strain. M. Iwami, et. al., J. Antibiotics 38, 835 (1985). New antitumor antibiotics FR-900405 and FR-900406.II. Production, isolation, characterization and antitumor activity. S. Kiyoto, et. al., J. Antibiotics, 38, 340 (1985).
3) PD 114759 and PD 115028, novel antitumor antibiotics with phenomenal potency. I. Isolation and characterization. R. H. Bunge, et. al., J. Antibiotics, 37, 1566 (1984) U.S. Pat. No. 4,554,162 (1985). Biological and biochemical activities of the novel antitumor antibiotic PD 114759 and related derivatives. D. W. Fry et. al., Investigational New Drugs, 4, 3 (19896).
4) New antibiotic complex CL-1577A, CL-1566B produced by Streptomyces sp. ATCC 39363. U.S. Pat. NO. 4,539,203 (1985).
5) CL-1577D and CL-1577E Antibiotic antitumor compounds, their production and use. U.S. Pat. No. 4,539,203.
6) CL-1724 Antibiotic compounds, their production and use. U.S. Pat. No. 4,554,162.
7) New antitumor antibiotics BBM-1675-A3 and BBM-1675-A4, obtained by fermentation of actinomadura verrucosospora strains H964-92 (ATCC 39334) or AB27Y (ATCC 39638). U.S. Pat. No. 4,675,187.
8) New N-acetyl-esperamicin A₁, A₂ and A₁ᵦ derivatives with antimicrobial and antitumor activities. European Patent 289,030.

All of the information regarding BBM-1675, FR-900405, FR-900406, PD 114759, PD 115028, CL-1577A, CL-1577B, CL-1577D, CL-1577E and CL-1724 contained in the above citations is incorporated herein by reference. The complete structures of esperamicins A₁, A₂, and A₁ᵦ (the BBM-1675 complex) and their respective N-acetyl derivatives have been reported, and these are included in Tables 1 and 2. The physical characteristics of the other above-named antitumor antibiotics indicate that they are all identical or very similar in structure to the esperamicins, and all contain a methyltrithio functional group.

As can be seen from the structures disclosed above, the α₁, α₂, α₃, α₄, β₁, β₂, γ₁, δ, and pseudoaglycone components of the LL-E33288 complex their dihydro and N-acyl counterparts, as well as the BBM-1675, FR-900405,k FR-900406, PD 114759, PD 115028, CL-1577A, CL-1577B, CL-1577D, CL-1577E and CL-1724 antibiotics and their N-acyl counterparts, each cor a methyltrithio group in their structure. The methyltrithio moiety of the above-named antibiotics is subject to displacement by a variety of thiol-containing organic molecules resulting in the formation of a new class of anticancer and antibacterial agents as described in our copending application No. 07/339,323.

It has now been discovered that the displacement of the methyltrithio unit of the compounds listed in Tables 1 and 2 as depicted in Scheme I can be used to introduce a spacer (Sp), the judicious choice of which enables the introduction of targeting units into the compounds of the above-named patents and applications.

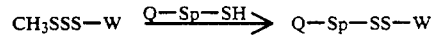

wherein Sp is a straight or branched-chain divalent or trivalent ($C_1-C_{18}$) radical, divalent or trivalent aryl or heteroaryl radical, divalent or trivalent ($C_3-C_{18}$) cycloalkyl or heterocycloalkyl radical, divalent or trivalent aryl- or heteroaryl-alkyl ($C_1-C_{18}$) radical, divalent or trivalent cycloalkyl- or heterocycloalkyl-alkyl ($C_1-C_{18}$) radical, or divalent or trivalent ($C_2-C_{18}$) unsaturated alkyl radical, wherein if Sp is a trivalent radical, it can be additionally substituted by amino, alkylamino, arylamino, heteroarylamino, carboxyl, lower alkoxy, hydroxy, thiol or lower alkylthio groups; Q is, or can be subsequently converted to, halogen, amino, alkylamino, carboxyl, carboxaldehyde, hydroxy, amino, alkylamino, carboxyl, carboxaldehyde, hydroxy, thiol, α-haloacetyloxy, lower alkyldicarboxyl, —CONHNH₂, —NHCONHNH₂, —NHCSNHNH₂, —ONH₂, —CON₃,

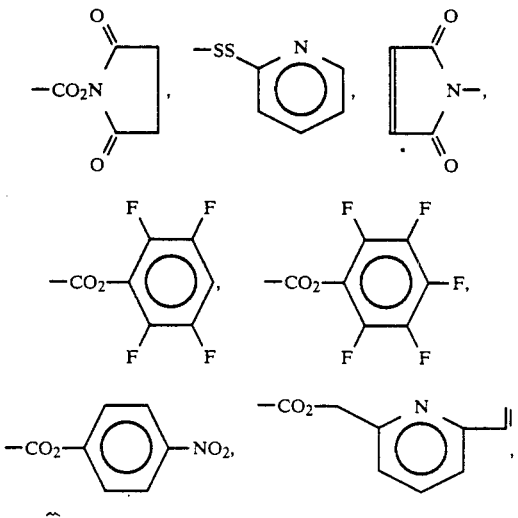

-continued

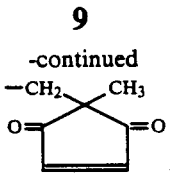

and W is as shown in Tables 1 and 2, above.

As long as the product from Scheme I contains at least one functional group which can be converted to, or is directly reactive with a targeting unit (Tu), targeted forms of the antitumor antibiotics of the above-named patents and applications can be generated, as shown in Scheme II below:

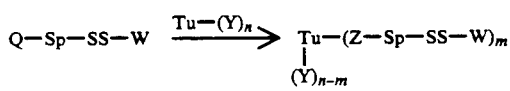

wherein Q, Sp, and W are as hereinbefore defined, Tu is a mono- or polyclonal antibody, its fragments, its chemically or genetically manipulated counterparts, or growth factors or steroids; Y is a side-chain amino, carboxy, or thiol group of a protein, an aldehyde derived from carbohydrate residues, or an amidoalkylthio group; n is an integer of from 1 to 100; Z is formed from covalent reaction of the groups Q and Y directly or after subsequent reduction and Z is —CONH—, —CONHN=CH—, —CONHNHCH$_2$—, —NHCONHN=CH—, —NHCONHNHCH$_2$—, —NHCSNHN=CH—, —NHCSNHNHCH$_2$—, —ON=CH—, —NH—, —NHCH$_2$—, —N=CH—, —CO$_2$—, —NHCH$_2$CO$_2$—, —SS—,

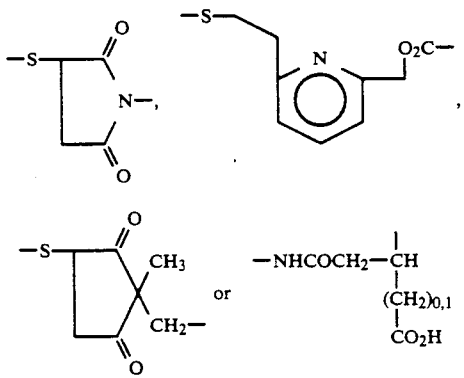

and m is 0.1 to 15.

As an example, and with reference to Scheme II, above, the 3-mercaptopropionic acid derivative of E-33288$\gamma_1^I$ (Q=CO$_2$H, Sp=—CH$_2$CH$_2$—), when converted to its activated hydroxysuccinimide form (Q=CO$_2$Su, Sp=—CH$_2$—CH$_2$—) can be used to react with some of the ε-amino groups of lysine residues (e.g., Tu=monoclonal antibody, Y=—NH$_2$ wherein n=50-100 from available lysine residues), at a pH between 7.0 and 9.5 in aqueous buffered solutions at temperatures between 4° C. to 40° C. to produce targeted forms of the antibiotics attached at random sites along the protein backbone (Tu=monoclonal antibody, Z=—NHCO—, Sp=—CH$_2$CH$_2$—, m=1-10). Only a fraction of the available lysine residues are substituted in this manner, since high loading is generally not considered compatible with preserving the antibody immunoreactivity. The same randomly-substituted immunoconjugates can also be prepared from the 3-mercaptopropionic acid derivative using other carboxyl group activating agents such as a variety of carbodiimides, or the corresponding acyl azide. Alternatively, a 3-mercaptopropionyl hydrazide derivative of E-33288$\gamma_1^I$ (Q=H$_2$NNHCO—, Sp=—CH$_2$CH$_2$—), when reacted with a periodate-oxidized antibody (tu=monoclonal antibody, Y=—CHO, N=1-15) as described in U.S. Pat. No. 4,671,958 at a pH between 4 and 7, in a buffered aqueous solution at a temperature of between 4° C. and 40° C., reacts only at the aldehyde functionality (derived from cleavage of vic-diols of carbohydrate residues situated on the Fc portion of the antibodies ) to generate monoclonal antibody conjugates containing the drug substituted at specific sites along the backbone of the protein (Tu=monoclonal antibody, Z=—CH=NNHCO—, Sp=—CH$_2$CH$_2$—, m=0.5-10). In order to block unreacted aldehyde groups on the antibody and thus avoid crosslinking, as well as stabilize the hydrolytically labile Schiff's base linkages, it is preferable (though not essential) to react the latter conjugate first with a compound such as acetyl hydrazide or tyrosine hydrazide, then reduce with sodium cyanoborohydride or sodium borohydride to produce the stabilize constructs of this invention (Tu=monoclonal antibody, Z=—CH$_2$NHNHCO—, Sp=—CH$_2$CH$_2$—, m=0.5-10). Other aldehyde-reactive groups as part of the drug construct are within our invention to generate the products of Scheme II. Such functional groups are preferably, though not limited to, those which react with aldehydes under acidic aqueous conditions. The reactivity of protein lysines under basic conditions is sufficiently great such that their amines compete with the products of Scheme II for available aldehydes of the monoclonal antibody. Alternative aldehyde-reactive groups are, for example, the semicarbazide, the thiosemicarbazide, and the O-substituted hydroxylamine functionalities.

Assembly of targeted forms of the compounds listed in Tables 1 and 2 is not restricted to the sequence outlined in Scheme II. The targeting unit (Tu) can be first modified to contain a thiol group, which is then reacted with the compounds of Tables 1 and 2 in accordance with Scheme III below:

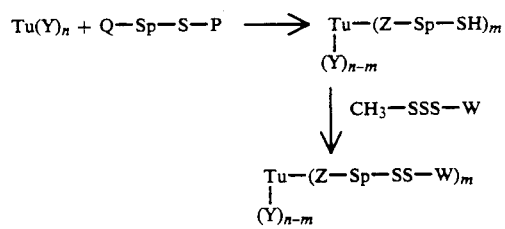

wherein Tu, Y, Q, Sp, W, n, and m are as hereinbefore defined, and P is hydrogen or 2-(pyridylthio), with the proviso that when Y is a thiol derived from a backbone amino acid residue of Tu, Z-Sp taken together is a covalent bond.

As an example, and with references to Scheme III, above, the monoclonal antibody can be reacted with 3-(2-dithiopyridyl)propionic acid hydroxysuccinimide ester to modify the protein through lysine residues (Tu=monoclonal antibody, Y=NH$_2$, n=50-100, Q=—CO$_2$Su, Sp=—CH$_2$—CH$_2$—, P=2-pyridylthio). Following reduction with, for example, dithiothreitol, an intermediate is generated (Tu=monoclonal antibody, Z=—NHCO—, Sp=—CH$_2$CH$_2$—, m=1 to 15) which can be reacted with the compounds of Tables 1 and 2 to generate the subject immunoconjugates. Similarly, 2-iminothiolane can be reacted with a monoclonal antibody to introduce thiol groups onto the surface of the protein directly, without requiring a reduction step (Tu=monoclonal antibody, Z=—NHCO—, Sp=—(CH$_2$)$_3$—, m=1 to 15), and this intermediate can be reacted with the compounds of Tables 1 and 2 as before. Alternatively, sulfhydryl groups inherent within the structure of monoclonal antibodies in dimeric form as cystine residues can be used to participate in the reaction of Scheme III directly. Such sulfhydryls are traditionally exposed by a combination of enzymatic digestion and reduction of native monoclonal antibodies (tu=Fab' fragment, Z—Sp=bond, Y=SH), but the use of genetically-altered constructs of monoclonal antibodies containing unpaired cystine residues is likewise contemplated.

A preferred embodiment of this invention is a protein-drug conjugate of the formula:

$$\text{Tu}-(Z-Sp-SS-W)_m$$
$$|$$
$$(Y)_{n-m}$$

prepared from the class of antitumor antibiotics designated LL-E33288 (CH$_3$SSS-W) comprising:

displacing the dithiomethyl moiety with a compound of formula Q-Sp-SH, wherein Sp is straight or branched-chain divalent or trivalent (C$_2$–C$_{10}$) radicals or divalent or trivalent (C$_2$–C$_5$) arylalkyl or heteroarylalkyl radicals, wherein if Sp is a trivalent radical, it can be additionally substituted by amino, heteroarylamino, hydroxy, or thiol groups; and Q is carboxyl, lower alkyldicarboxyl anhydride, —CO$_2$Su, —CONHNH$_2$, or

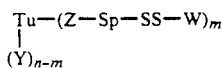

to produce an intermediate of general formula Q-Sp-SS-W, wherein Q, Sp, and W are as hereinbefore defined, Reacting Q-Sp-SS-W with a molecule of the formula Tu-(Y)$_n$ wherein Tu is a monoclonal antibody which exhibits preferential reactivity with a human tumor-associated antigen, Y is a side-chain amino group on the antibody, or an aldehyde generated by oxidation of the carbohydrate groups of the antibody, and n is an integer of from 1 to 100, to produce a compound of the formula:

$$\text{Tu}-(Z-Sp-SS-W)_m$$
$$|$$
$$(Y)_{n-m}$$

wherein Tu, Y, Sp, W, and n are as hereinbefore defined, and Z is formed from covalent reaction of the groups Q and Y directly or after subsequent reduction, and Z is —CONH—, —CONHN=CH—, —CONHNHCH$_2$—, or

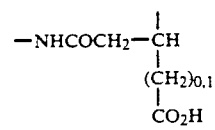

and m is 0.1 to 15.

A number of different monoclonal antibodies (MoAbs) are used to exemplify targeting of the methyltrithio anticancer compounds. MoAbs Lym 1 and Lym 2 recognize different antigens on mature B-lymphocytes and their product lymphomas. The production and characteristics of these MoAbs are described by A. L. Epstein, et. al., "Cancer Research" 47, 830 (1987). MoAb B72.3 targets primarily to carcinomas of the breast and colon, though reactivity with pancreatic, ovarian, and lung carcinomas has also been noted. The antibody has been described by T. L. Lug, et. al., "Int. J. Cancer" 38, 661 (1986). MoAb CT-M-01, which recognizes primarily breast tumors is described in EPO application 86 401482.4 filed July 3, 1986 and MAC-68 is produced by a sub-clone of the hybridoma which produces CT-M-01, and recognizes both breast and colon carcinomas. Intermediates of the subject compounds useful for, and conjugates with these antibodies, are described in the experimental section. It should not, however, be construed that this patent is limited to or restricted by the aforementioned antibodies. Instead, the methodology is sufficiently general that it can be applied to all antibodies regardless of their class or isotype, their enzymatically-derived fragments, their chemically manipulated and stabilized fragments, as well as their respective chimeric and humanized counterparts. Nor are the targeting units restricted only to monoclonal antibodies. Other proteins, as well as small molecules for which receptors exist on target issues, are within the purview of our discovery as targeting entities.

The methods of this invention used to produce monoclonal antibody conjugates form the compounds of Tables 1 and 2 yield constructs which retain good immunoreactivity with target cell lines, as determined by the following in vitro assays:

TARGET CELLS

All target cells were maintained in RPMI 1640 media supplemented with 5% Fetal Calf Serum (FCS), ITS (Collaborative Research, Cat #40351), streptomycin (50 μg/ml), penicillin (50 units/ml), gentamycin sulfate (50 μg/ml) and glutamine (0.03%). The cells were maintained in a humidified 5% CO$_2$ incubator at 37° C.

I. IMMUNOREACTIVITY ASSAYS

Procedure I—Elisa

Appropriate target cells were harvested, counted and suspended in Dulbecco's Phosphate Buffered Saline (DPBS) at an optimal concentration for monoclonal antibody (MoAb) being tested. 0.1 ml of cells were aliquoted in each well of a sterile tissue culture polystyrene 96-well plate. The plates were centrifuged for 5 minutes at 1,000 RPM's and the supernatant was flicked off. Plates were air-dried overnight and may be stored at 4° C. for up to 3 months.

Non-specific binding sites were blocked by adding 200 μl of 1% gelatin in DPBS per well and incubating the plate for 1 hour at 37° C. in a humid incubator. (All subsequent incubations are done under similar conditions). The plates were washed once with 250 μl of 0.5% TWEEN-20 in DPBS (washing solution) using the automated ELISA washing system for Dynatech (Ultrawash II). Samples to be tested were diluted to make a final concentration of 3 μg/ml MoAb equivalents in 0.1% gelatin-DPBS. Six additional threefold serial dilutions were prepared from each 3 μg/ml sample and 100 μl was added to appropriate wells in triplicate. The bottom row of wells only received 100 μl of 0.1% gelatin as background. Plates were incubated for 45 minutes and then washed three times. Alkaline phosphates conjugated affinity purified goat anti-mouse immunoglobulins (Cappel Cat#8611-0231) was diluted 1:125 in 0.1% gelatin and 100 μl was added to each well. Plates were incubated for 45 minutes and then washed three times. 200 μl of p-nitrophenyl phosphate substrate solution (see below) was added to each well. After 45 minutes at room temperature the reaction was stopped by the addition of 50 μl of 3 M NaOH. The absorbance of the contents of each well was read at 405 nm in the automated spectrophotometer from Dynatech (EIA Autoreader #EL-310).

Substrate Diethanolamine Buffer (10%)

97 ml diethanolamine
800 ml water
0.2 grams $NaN_3$
100 mg $MgCl_2$ $6H_2O$

The reagents were dissolved by continuous stirring and 1 M HCl was added under the pH was 9.8. The total volume was made up to 1 liter with water and filter sterilized with a 0.2 μ filter. The buffer was stored in the dark at 4° C. Immediately before use, p-nitrophenyl phosphate (Sigma, Cat#104-40) was dissolved in the 10% diethanolamine buffer (must be at room temperature) to give a final concentration of 1 mg/ml.

Calculation of O. D. Values

The percentage binding of each sample was calculated by the following equation:

$$\frac{A - B}{C - B} \times 100 = \% \text{ Binding}$$

A = Average O.D. of test sample
B = Average O.D. of background
C = Average O.D. of 3 μg/ml unmanipulated MoAb control The % binding was plotted on the non-log scale of a semi-log graph and the MoAb concentration was plotted on the log scale. The $BD_{50}$ (i.e. dose of antibody needed to give 50% binding) of each test sample was derived form the graph and the amount of retention of immunoreactivity was calculated by the following equation:

$$\frac{BD_{50} \text{ of MoAb control}}{BD_{50} \text{ of test sample}} \times 100 = \% \text{ Immunoreactivity retained}$$

Procedure 2—Indirect RIA

Appropriate amounts of target cells in 0.2 ml of 10% FCS media were aliquoted into 4 ml polystyrene tubes. Samples to be tested were diluted to a concentration of 2 μg/ml MoAb equivalents in 10% FCS media. Five three-fold serial dilutions were prepared from each 2 μg/ml sample and 0.2 ml was added to each tube in duplicate. Background samples received only cells and media. Cells were incubated at 4° C. for 1 hour, then washed 2 times (all RIA washes were done with a 3 ml volume) with 2% FCS media. 0.05 ml of sheep F(ab')$_2$ anti-mouse IgG [$^{125}$I] (DuPont, Cat# NEX 162-0142) containing approximately 500,000 CPM's was added to each tube; cells were incubated an additional hour at 4° C., washed once with 2% FCS and twice with PBS. 0.5 ml of PBS was added to each tube, cells were vortexed, transferred to clean tubes and counted for 1 minute in a Packard Gamma 500.

The % binding of each value was determined and graphed like the preceding ELISA equation, except CPM's were substituted for O.D. units and C=Average CPM's of 1 μg/ml unmanipulated MoAb control The % immunoreactivity retained of each sample was calculated as previously discussed.

Procedure 3—Direct RIA

Appropriate amounts of target cells in 1 ml of 10% FCS media were aliquoted into 4 ml polystyrene test tubes, centrifuged and supernatant was discarded. Samples to be tested were diluted to make a concentration of 200 μg/ml MoAb equivalents in 10% FCS media. Five additional five-fold serial dilutions were prepared from each 200 μg/ml sample and 0.05 ml was added to each tube in duplicate. 0.05 ml of $^{125}$I-MoAb was added to each tube (optimal amount is individually determined for each MoAb and batch). Positive control samples contained cells, media and $^{125}$I-MoAb. Background samples contained non-specific cells, media and $^{125}$I-MoAb. Cells were incubated for 1 hour at 4° C., washed once with 2% FCS media, twice with PBS, transferred and counted as previously mentioned.

The % $^{125}$I-MoAb binding inhibition of each sample was calculated by the following formula:

$$\frac{A - B}{C - B} \times 100 = \%^{125}I\text{-MoAb Binding inhibition}$$

A = Average CPM's of sample
B = Average CPM's of background
C = Average CPM's of positive control The plot and % immunoreactivity retained by each sample was calculated as previously discussed except the $BD_{50}$ is actually $BID_{50}$ (Dose of MoAb needed to give 50% inhibition of the binding of $^{125}$I-MoAb).

Notes

1) Tubes were always vigorously vortexed immediately after the addition of every reagent in the RIA's.
2) An internal control sample equalling 50% of the unmanipulated MoAb control was included in each set of assays to confirm whether each procedure was quantitative in predicting the conjugates' retention of immunoreactivity.

The results from these assays are tabulated below in Table 3.

TABLE 3

| Immunoreactivity of MoAb Congugates | | |
|---|---|---|
| | Preparation | Immunoreactivity % of unmodified MoAb control |
| Non-specific conjugates using the product of Example 3 with: | | |
| Lym 1 | #1 | 15 |

TABLE 3-continued

Immunoreactivity of MoAb Conjugates

| | Preparation | Immunoreactivity % of unmodified MoAb control |
|---|---|---|
| B72.3 | #1 | 70 |
| | #2 | 10 |
| Hydrazide of 3-mercaptopropionic acid disulfide of LLE33288$\gamma_1^I$ (Example 4) congugated to: | | |
| Lym 1 | #1 | 100 |
| | #2 | 87 |
| | #3 | 64 |
| | #4 | 80 |
| | #5 | 100 |
| Hydrazide of 3-mercaptopropionic acid disulfide of E33288$\gamma_1^I$ (Example 4) conjugated to: | | |
| Lym 2 | #1 | 57 |
| | #2 | 85 |
| | #3 | 39 |
| | #4 | 70 |
| B72.3 | #1 | 100 |
| | #2 | 90 |
| CT-M-01 | #1 | 60 |
| MAC-68 | #1 | 40 |
| | #2 | 28 |
| Hydrazide conjugates prepared using the product of Example 5 with: | | |
| Lym 1 | #1 | 100 |
| | #2 | 100 |
| Hydrazide of 3-mercaptopropionic acid disulfide of LL-E33288$\alpha_3^I$ (Example 6) conjugated to: | | |
| Lym 1 | | 78 |
| CT-M-01 | | 81 |
| Hydrazide of 3-mercaptopropionic acid disulfide of N-acetyl LL-E33288$\delta_1^I$ (Example 7) conjugated to: | | |
| Lym 1 | | 82 |
| CT-M-01 | | 100 |
| B72.3 | | 100 |
| Hydrazide of 3-mercaptopropionic acid disulfide of LL-E33288$\alpha_2^I$ (Example 8) conjugated to: | | |
| CT-M-01 | | 56 |
| Hydrazide of 3-mercaptopropionic acid disulfide of iodo LL-E33288 pseudoaglycone (Example 9) conjugated to: | | |
| CT-M-01 | | 50 |
| Hydrazide of 3-mercaptobutyric acid disulfide of LL-E33288$\delta_1^I$ (Example 10) conjugated to: | | |
| Lym-1 | | 73 |
| Hydrazide of 3-mercaptoisovaleric acid disulfide of LL-E33288$\delta_1^I$ (Example 11) conjugated to: | | |
| Lym-1 | | 64% |
| Hydrazide of p-mercaptodihydrocinnamic acid disulfide of LL-E33288$\delta_1^I$ (Example 12) conjugated to: | | |
| Lym-1 | | 61% |

The monoclonal antibody conjugates of this invention are active as anticancer agents. The assay described below for assessing in vitro cytotoxicity shows the dramatic preference of the constructs for target cell lines as opposed to non-target cells, and provides a measure of utility of targeted forms of the compounds compared to their non-targeted counterparts.

Cytotoxicity Assays

In Vitro

Samples to be tested were diluted to a concentration of 0.2 or 0.02 μg/ml of parent drug equivalents (starting concentration is dependent on cell line to be tested and potency of the parent drug). Three or four additional five-fold dilutions were prepared from each original sample dilution and 0.2 ml was added to sterile 15 ml polystyrene tubes. At least one similar conjugate consisting of parent drug and an irrelevant MoAb was included in each assay to determine specificity of the relevant conjugate. $10^5$ appropriate target cells in 0.2 ml of 10% FCS media were aliquoted into the tubes and vortexed. In addition, an identical test was performed utilizing irrelevant cells as targets to further confirm specificity of relevant conjugate. MoAb controls received only equivalent amounts of MoAb and positive control samples received only 10% FCS media.

Cells were incubated at 37° C. for 7 minutes then washed 4 times with 8 ml of 2% FCS media. 0.1 ml of 10% FCS was added to each tube, cells were vortexed and 0.2 ml was aliquoted to each well of a sterile 96-well polystyrene tissue culture plate.

Plates were incubated for 2 days in a humidified 37° C. incubator with 5% $CO_2$. One half of the media was removed and replaced with fresh media containing 2 μCi/ml $^3$H thymidine (DuPont, NEN, Cat# NET-027). Incubation was continued for 24 hours, cells were frozen, thawed and harvested by a PHD cell harvester (Cambridge Technology, Inc.). Each sample was counted for 1 minute in a Beckman LS 5800 scintillation counter on Channel 1.

The % growth inhibition was calculated as follows:

$$\frac{\text{Average } CPM \text{ of test value}}{\text{Average } CPM \text{ of media control}} \times 100 = \% \text{ Growth}$$

$$100 - \% \text{ Growth} = \% \text{ Inhibition}$$

The % inhibition was plotted on the non-log scale of the semi-log graph and the parent drug concentration was plotted on the log scale. The $IC_{50}$ (concentration of parent drug needed to give 50% inhibition) of each test sample was derived from the graph and the amount of retention of cytotoxicity was calculated by the following equation:

$$\frac{IC_{50} \text{ of parent drug}}{IC_{50} \text{ of test sample}} \times 100 = \% \text{ Cytotoxicity Retained}$$

The results from the in vitro cytotoxicity assay are tabulated below in Table 4.

nomas (CA73, Ovcar-3), breast carcinoma (MS-1) and colon carcinoma (LS174T) were propagated in athymic

TABLE 4

In vitro Cytotoxicity of Moab Conjugates

| | MoAb | Preparation | Cytotoxicity | |
|---|---|---|---|---|
| Non-specific conjugates prepared using product of Example 3 with: | | | % E33288$\gamma_1^I$ | % product of Example 1 |
| | Lym 1 | #1 | .9 | 11.3 |
| | B72.3 | | 1.4 | 3.8 |
| Hydrazide conjugates prepared using product of Example 4 with: | | | % E33288$\gamma_1^I$ | % product of Example 4 |
| | Lym 1 | #1 | | 80 |
| | | #2 | 56 | 191 |
| | | #3 | 40 | 60 |
| Hydrazide conjugates prepared using product of Example 4 with: | | | % E33288$\gamma_1^I$ | % product of Example 4 |
| | Lym 1 | (#3 Against non-targeted cells) | 0 | 0 |
| | Lym 2 | #1 | | 29 |
| | | #2 | 2 | 100 |
| | | #3 | 2 | 55 |
| | B72.3 | #1 | 0 | 0 |
| | | #2 | 0 | 0 |
| | MAC-68 | #1 | | 90 |
| | CT-M-01 | #1 | 111 | 830 |
| Hydrazide conjugates prepared using product of Example 5 with: | | | % E33288$\gamma_1^I$ | |
| | Lym 1 | #1 | 300 | |
| | | #2 | 100 | |

| | MoAb | Cytotoxicity |
|---|---|---|
| Hydrazide conjugate prepared using product of Example 6 with: | | % LL-E33288$\alpha_3^I$ |
| | Lym 1 | 500 |
| | CT-M-01 | 300 |
| Hydrazide conjugate prepared using product of Example 7 with: | | % N-acetyl LL-E33288$\delta_1^I$ |
| | Lym 1 | 400 |
| | CT-M-01 | 700 |
| Hydrazide conjugate prepared using product of Example 8 with: | | % product of Example 8 |
| | CT-M-01 | −18 |
| Hydrazide conjugate prepared using product of Example 9 with: | | % product of Example 9 |
| | CT-M-01 | 100 |
| Hydrazide conjugate prepared using product of Example 10 with: | | % product of Example 10 |
| | Lym 1 | 400 |
| Hydrazide conjugate prepared using product of Example 11 with: | | % product of Example 11 |
| | Lym 1 | 320 |
| Hydrazide conjugate prepared using product of Example 12 with: | | % product of Example 12 |
| | Lym 1 | 560 |

The following assay system was used to measure the in vivo activity of the conjugates of this invention.

In vivo tests for antitumor activity on drug-monoclonal antibody conjugates were done using human tumor xenographs in athymic (nude) mice.

Burkitt lymphoma (Raji) and myeloma (HS Sultan) cells were harvested from culture flasks and inoculated subcutaneously ($\geq 80 \times 10^6$ Raji cells or $40 \times 10^6$ HS Sultan cells) into test mice. Solid tumors, ovarian carcinomas (CA73, Ovcar-3), breast carcinoma (MS-1) and colon carcinoma (LS174T) were propagated in athymic mice, removed, cut into 2 mm³ fragments and implanted subcutaneously into test mice (5—8 fragments per mouse).

Drugs, monoclonal antibodies and drug-monoclonal antibody conjugates were administered intrapertioneally once each 3 days for 3 or 5 total injections starting on day 2, 3, 4, 6, 7 or 8 days after tumor implantation. Tumor measurements (the length of width of the tumor) were made by means of a Fowler ultra CAL II electronic caliper each 7 days for 4 to 6 weeks post tumor implantation. Tumor mass in mg was estimated from the formula:

$$\frac{Length(mm) \times Width(mm)}{2}$$

Tumor growth inhibition was calculated for each test group on a percent of control [mean mg of treated (T) divided by mean mg of control (C)×100]. A T/C value $\geq 42\%$ in groups with $\geq 65\%$ surviving animals is considered necessary to demonstrate activity.

The results from this assay appear in Table 5.

TABLE 5

In vivo Antitumor Testing Results

| | Dosage (mcg) | | Tumor size | |
|---|---|---|---|---|
| | MoAb | Drug | (T/C) % control | S/T |
| Hydrazide of 3-mercaptopropionic acid disulfide of LL-E33288$\gamma_1^I$ conjugated to Lym 2 | 14.5 | 0.26 | 12 | 5/6 |
| Hydrazide alone | — | 0.26 | 34 | 4/6 |
| MoAb Lym 2 alone | 14.5 | — | 32 | 6/6 |
| Mixture, hydrazide + MoAb Lym 2 | 14.5 | 0.26 | 20 | 5/6 |
| ip treatment against human melanoma cell line H. S. Sultan, 3 injections starting on day 5 after tumor implantation. measurements given made on day 35 post-implantation | | | | |
| Hydrazide of 3-mercaptopropionic acid disulfide of LL-E33288$\gamma_1^I$ conjugated to MAC-68 | 15.5 | 0.25 | 39 | 7/7 |
| Hydrazide alone | — | 0.25 | — | 0/6 |
| MoAb MAC-68 alone | 31 | — | 78 | 6/6 |
| Mixture, hydrazide + MoAb MAC-68 | 15.5 | 0.25 | — | 0/6 |
| Melphalan (as positive control) | — | 200 | 43 | 6/6 |
| ip treatment against human ovarian cancer line CA73. three injections started 3 days after tumor implantation, measurements given made on day 35 post-implantation | | | | |
| Hydrazide of 3-mercaptopropionic acid disulfide of LL-E33288$\gamma_1^I$ conjugated to CT-M-01 | 8.75 | 0.25 | 14 | 4/6 |
| Hydrazide alone | — | 0.25 | — | 0/6 |
| MoAb CT-M-01 alone | 8.75 | — | 75 | 5/6 |
| Mixture, hydrazide + MoAb CT-M-01 | 8.75 | 0.25 | — | 0/6 |
| Vincristine (positive control) | — | 20 | 0 | 4/4 |
| ip treatment against human breast cancer cell line MX-1, three injections started on day 2 following tumor implantation, measurements given made on day 35 post-implantation | | | | |
| Hydrazide of 3-mercaptopropionic acid disulfide of LL-E33288$\gamma_1^I$ conjugated to B72.3 | 6.2 | 0.125 | 62 | 6/6 |
| Hydrazide alone | — | 0.125 | 85 | 6/6 |
| MoAb B72.3 alone | 6.2 | — | 96 | 6/6 |
| Mixture, hydrazide + MoAb B72.3 | 6.2 | 0.125 | 105 | 5/6 |
| LL-E33288$\gamma_1^I$ (3 treatments) | — | 0.005 | 141 | 5/6 |
| Cis platinum (positive control, 3 treatments) | — | 60 | 6 | 6/6 |
| ip treatments against human ovarian cell line OVCAR-3, five injections starting on day 4 after tumor implantation (unless otherwise noted), measurements given made on day 35 post-implantation | | | | |
| Hydrazide of 3-mercaptopropionic acid disulfide of LL-E33288$\gamma_1^I$ conjugated to Lym 1 | 27 | 0.26 | 6 | 3/6 |
| Hydrazide alone | — | 0.26 | 72 | 6/6 |
| MoAb Lym 1 alone | 27 | — | 72 | 6/6 |
| Mixture, hydrazide + MoAb Lym 1 | 13 | 0.13 | 61 | 4/6 |
| ip treatment against human Burkitt lymphoma cell line Raji TC, three injections started on day 7 after tumor implantation, measurements given made on day 28 post-implantation | | | | |
| Hydrazide of 3-mercapto- | 28 | 0.75 | 1.3 | 6/6 |

TABLE 5-continued

| | In vivo Antitumor Testing Results | | | |
|---|---|---|---|---|
| | Dosage (mcg) | | Tumor size | |
| | MoAb | Drug | (T/C) % control | S/T |
| propionic acid disulfide of LL-E33288α₃$^I$ conjugated to Lym 1 | | | | |
| LL-E33288α₃$^I$ alone | — | 0.75 | 365 | 6/6 |
| Hydrazide alone | — | 0.75 | 330 | 6/6 |
| MoAb Lym alone | 28 | — | 68 | 6/6 |
| ip treatment against human Burkitt lympoma cell line Raji TC, three injections started on day 7 after tumor implantation, measurements given made on day 28 post-implantation | | | | |
| Hydrazide of 3-mercapto-propionic acid disulfide of LL-E33288α₃$^I$ conjugated to CT-M-01 | 83 | 2.0 | 0.02 | 6/6 |
| LL-E33288α₃$^I$ alone | — | 2.0 | — | 0/6 |
| MoAb CT-M-01 alone | 83 | — | 75 | 5/6 |
| Vincristine (positive control | — | 20 | 1.2 | 5/5 |
| ip treatment against human breast cancer cell line MX01, three injections started on day 2 following tumor implantation, measurements given made on day 35 post-implantation. | | | | |
| Hydrazide of N-[[(4-methylcoumarin-7-yl)-amino]acetyl]cysteine disulfide of LL-E33288δ₁$^I$ conjugated to Lym 1 | 50 | 0.22 | 23 | 7/7 |
| Hydrazide alone | — | 0.22 | 228 | 4/7 |
| MoAb Lym 1 alone | 50 | — | 61 | 7/7 |
| Mixture, hydrazide plus MoAb Lym 1 | 50 | 0.22 | 56 | 7/7 |
| ip treatment against human Burkitt lymphoma cell line Raji TC, three injections started on day 7 after tumor implantation, measurements given made on day 35 post-implantation | | | | |
| Hydrazide of 3-mercapto-propionic acid disulfide of N-Acetyl LL-E33288δ₁$^I$ conjugated to CT-M-01 | 125 | 1.0 | 0 | 6/6 |
| Hydrazide alone | — | 2.0 | 71 | 3/6 |
| Mixture, N-acetyl LL-E33288δ₁$^I$ plus MoAb CT-M-01 | 125 | 1.0 | 5 | 1/6 |
| N-acetyl LL-E33288δ₁$^I$ | — | 1.0 | 46 | 2/6 |
| iv treatment against human breast cancer cell line MX-1, three injections starting on day 2 following tumor implantation, measurements given made on day 42 post-implantation | | | | |
| Hydrazide of 3-mercapto-propionic acid disulfide of N-acetyl LL-E33288δ₁$^I$ conjugated to Lym 1 | 37 | 1.0 | 11 | 6/6 |
| Hydrazide alone | — | 1.0 | 517 | 6/6 |
| N-acetyl LL-E33288δ₁$^I$ alone | — | 0.5 | 226 | 6/6 |
| MoAb Lym 1 alone | 37 | — | 178 | 6/6 |
| iv treatment against human Burkitt lymphoma cell line Raji TC, three injections starting on day 7 after tumor implantation, measurements given made on day 35 post-implantation | | | | |
| Hydrazide of 3-mercapto-propionic acid disulfide of N-acetyl LL-E33288δ₁$^I$ conjugated to B72.3 | 127 | 2.7 | 61 | 6/6 |
| N-acetyl LL-E33288δ₁$^I$ alone | — | 2.0 | 32 | 1/6 |
| MoAb B72.3 alone | 127 | — | 125 | 6/6 |
| Vincristine (positive control) | — | 20 | 23 | 6/6 |
| iv treatment against human colon cancer cell line LS174T, three injections started on day 8 following tumor implantation, measurements given made on day 21 post-implantation | | | | |
| Hydrazide of 3-mercapto-propionic acid disulfide | 112 | 2.7 | 40 | 5/6 |

TABLE 5-continued

| | In vivo Antitumor Testing Results | | | |
|---|---|---|---|---|
| | Dosage (mcg) | | Tumor size | |
| | MoAb | Drug | (T/C) % control | S/T |
| of N-acetyl LL-E33288$\delta_1^I$ conjugated to CT-M-01 | | | | |
| N-acetyl LL-E33288$\delta_1^I$ alone | — | 2.0 | 32 | 1/6 |
| Vincristine (positive control) | — | 20 | 23 | 6/6 |
| iv treatment against human colon carcinoma line LS174T, three injections started 8 days after tumor implantation, measurements given made on day 21 post-implantation | | | | |
| Hydrazide of 3-mercapto-propionic acid disulfide of LL-E33288$\alpha_2^I$ conjugated to CT-M-01 | 24 | 1.0 | 0.33 | 2/6 |
| Hydrazide alone | — | 1.0 | — | 0/6 |
| iv treatment against human breast cancer cell line MX-1, three injections started on day 2 following tumor implantation, measurements given made on day 35 post-implantation | | | | |

The invention will be further described in conjunction with the following non-limiting examples.

EXAMPLE 1

3-Mercaptopropionic Acid Disulfide of LL-E33288$\gamma_1^I$

To a solution of 90 mg of LL-E33288$\gamma_1^I$ in 3-mercaptopropionic acid in 1 ml of acetonitrile. The solution was vortexed and then stored at −20° C. for 6 days. The solvent was removed in vacuo and the residue chromatographed over 10 ml of silica gel in methylene chloride. The column was developed with 50 ml of methylene chloride, 50 ml of 4% methanol in methylene chloride and finally 100 ml of 8% methanol in methylene chloride. Evaporation of this last fraction gave a residue which was taken up in ethyl acetate with the aid of a little acetone and added dropwise to an excess of hexane. The precipitate was collected and dried, giving 39 mg of the desired product (FABMS, M+H 1394).

EXAMPLE 2 p-Nitrophenyl 3-mercaptopropionic acid disulfide of LL-E33288$\gamma_1^I$ (A) Preparation of p-nitrophenyl ester of 3-mercaptopropionic acid Commercial 3-mercaptopropionic acid in methylene chloride containing a catalytic amount of concentrated sulfuric acid was treated with isobutylene for 20 minutes. The solution was then extracted with 1N sodium bicarbonate solution after which the methylene chloride solution was dried using anhydrous magnesium sulfate. The solution was then evaporated to a colorless mobile liquid which NMR and mass spectral data indicated was the S-t-butylmercaptopropionic acid, t-butyl ester.

An aliquot of this ester was refluxed with 6N hydrochloric acid in dioxane for 2.5 hours. The solvent was evaporated, ethyl acetate was added and this solution was extracted with sodium carbonate. The sodium carbonate extract was treated with 6N hydrochloric acid until the pH of the suspension was 2.0. The suspension was then extracted with ethyl acetate, the extract dried over anhydrous magnesium sulfate and the solvent evaporated to a colorless liquid which $^1$H NMR and mass spectral data indicated was S-t-butylmercaptopropionic acid.

This compound was converted to the p-nitrophenyl ester by treatment with equimolar amounts of p-nitrophenol and dicyclohexylcarbodiimide in tetrahydrofuran for 4 hours. The dicyclohexyl urea by-product was removed by filtration and the filtrate was evaporated to an oil which was purified by passage over neutral silica gel using the solvent system hexane:methylene chloride (50:50). The pure p-nitrophenyl ester derivative was a faintly yellow, mobile oil.

The free mercaptan was unmasked by the following procedure. The S-t-butylmercaptopropionic acid p-nitrophenyl ester was dissolved in trifluoroacetic acid and a slight molar excess (10%) of mercuric acetate was added. The mixture was stirred for 30 minutes, then the trifluoroacetic acid was evaporated and the residue taken up in dimethylformamide. This solution was treated with hydrogen sulfide gas for 15 minutes, then the black mercuric sulfide was filtered off and the filtrate evaporated under reduced pressure to eliminate up to 99% of the dimethylformamide. The resultant slightly brownish mobile liquid was purified over neutral silica gel using hexane:methylene chloride (50:50). The major component was shown by $^1$H NMR to contain a small amount of the t-butyl mercapto derivative. Analytical HPLC over two Perkin-Elmer Pecosphere $C_{18}$ columns in tandem [4.6×33 mm and 4.6×83 mm] using a gradient system of 37.5/62.5 to 47.5/52.5 of acetonitrile and 0.1 M ammonium acetate buffer at pH 6.5 (acetic acid) over a 12 minute span indicated that the product was 88% of the p-nitrophenyl ester of 3-mercaptopropionic acid and 10% of the less polar S-t-butylmercaptopropionic acid p-nitrophenyl ester. There was also a small amount of free p-nitrophenol present.

(B) Reaction of p-nitrophenyl ester of 3-mercaptopropionic acid with LL-E33288$\gamma_1^I$ A 100 mg portion of LL-E33288$\gamma_1^I$ was dissolved in 50 ml of acetonitrile. To this was added a solution of 25.7 mg of p-nitrophenyl ester of 3-mercaptopropionic acid in 1 ml of acetonitrile. The reaction was left at −20° C. for 48 hours. HPLC indicated the reaction was complete. The solution was evaporated to dryness and the residue taken up in 4-5 ml of ethyl acetate using sonication to effect solution. The mixture was filtered and the filtrate dripped into 45 ml of stirred hexane. The resultant faintly yellow solid was collected and dried under reduced pressure, giving 93 mg of the p-nitrophenyl ester of propionic acid derivative of LL-E33288$\gamma_1^I$ as established by $^1$H NMR. By FABMS the [M+H] ion appeared at m/s=1515.

Retention time on $C_{18}$ reverse phase HPLC:18 min. with 50% acetonitrile/0.1 M aqueous ammonium acetate (LL-E33288$\delta_1^I$:8.0 min., ester hydrolysis product:1.5 min.).

EXAMPLE 3

N-Hydroxysuccinimidyl 3-mercaptopropionate disulfide of LL-E33288$\gamma_1^I$ To a solution of 5 mg of the 3-mercaptopropionic acid disulfide analog of LL-E33288$\gamma_1^I$ from Example 1 in 0.5 ml of tetrahydrofuran was added 0.45 mg of N-hydroxysuccinimide in 0.1 ml of tetrahydrofuran and then 1.8 mg of dicyclohexylcarbodiimide in 0.2 ml of tetrahydrofuran. The reaction was allowed to stir at room temperature for 4 hours and was then quenched with a large excess of hexanes. The solid was isolated by filtration and dissolved in ethyl acetate. The resulting solution was washed three times with brine, dried with magnesium sulfate, and evaporated to 5 mg of the desired product as a tan powder which was used without further purification. Retention time on reverse phase $C_{18}$ HPLC: 15 minutes with 40% acetonitrile/0.1 M aqueous ammonium acetate (starting material: 6.0 minutes).

EXAMPLE 4

3-Mercaptopropionyl hydrazide disulfide of LL-E33288$\gamma_1^I$

To 5.4 ml (3 eq) of anhydrous hydrazine in 100 ml of refluxing tetrahydrofuran under argon was added dropwise 9.2 ml (83 mmol) of methyl 3-mercaptopropionate in 50 ml tetrahydrofuran over 2 hours. The solution was refluxed an additional two hours, evaporated, and then diluted and evaporated twice from 300 ml of toluene. The product was applied to a plug of silica gel with 5% ethyl acetate/chloroform and eluted from the plug with 20% methanol/chloroform. The resultant 3-mercaptopropionyl hydrazide was a faintly pink oil which solidified when cooled but melted at room temperature.

To 50 mg of LL-E33288$\delta_1^I$ in 50 ml of acetonitrile at $-15°$ C. was added 6.6 mg of 3-mercaptopropionyl hydrazide in 1 ml tetrahydrofuran. One equivalent of triethylamine or one equivalent of triethylamine and one equivalent of acetic acid was added. The reaction was allowed to stir at 0° C. for one hour and the solvent was then evaporated. The residue was chromatographed on silica gel with a 10–15% methanol-in-chloroform gradient to yield 26 mg of the desired product. FABMS, m/s=1408 (M+H); retention time on reverse phase $C_{18}$ HPLC: 5.0 minutes in 41% acetonitrile/0.1 M aqueous ammonium acetate.

EXAMPLE 5

N-[[(4-Methyl-coumarin-7-yl)amino]acetyl]cysteine hydrazide disulfide of LL-E33288$\gamma_1^I$ A mixture of 1.0 g (5.7 mmol) of 4-methyl-7-aminocoumarin, 3.0 ml of ethyl bromoacetate (5 eq), 90 mg (0.1 eq) of sodium iodide, and 30 ml dimethylformamide was heated under argon at 80° C. for 5 hours. The mixture was cooled, diluted with ethyl ether, washed three times with 50% brine, dried with magnesium sulfate, and evaporated to dryness. The crude product was dissolved in chloroform containing 1% ethyl acetate and filtered through a plug of silica gel. Recrystallization from diethyl ether containing a trace of chloroform yielded pure ethyl N-[(4-methyl-coumarin-7-yl)amino]acetate.

To 1.96 g (7.5 mmol) of the above ester in 15 ml of methanol and 15 ml of tetrahydrofuran was added B 10 ml of 1N aqueous sodium hydroxide. After 30 minutes, 4 ml of 10% aqueous hydrochloric acid was added. The organic solvents were evaporated and the resultant crystalline product was filtered and washed with cold ethanol and then ether. This material was dissolved in 20 ml of tetrahydrofuran and 4 ml of dimethylformamide. Dicyclohexylcarbonyldiimidazole (1.3 g, 2.2 eq) was added and the reaction allowed to stir for 15 minutes. Cysteine ethyl ester hydrochloride (1.6 g, 2.5 eq) and triethylamine (1.2 ml) were then added. After a further three hours, the reaction was diluted with ethyl ether containing 5% methylene chloride and washed once with 10% aqueous hydrochloric acid and twice with brine. After drying with magnesium sulfate and evaporating the solvents, the crude product was crystallized by dissolving in chloroform containing a minimal amount of ethanol and then added an excess of ether. The crystals were filtered and dried to give pure N-[[(4-methyl-coumarin-7-yl)amino]acetyl]cysteine ethyl ester.

A mixture of 5 ml of chloroform, 20 ml of methanol, and 0.4 ml of hydrazine hydrate was heated to reflux under argon. To this was added 550 mg of N-[[(4-methyl-coumarin-7-yl)amino]acetyl]cysteine ethyl ester. After refluxing for 9 hours the mixture was cooled and the solid product was filtered and washed with chloroform and then ethyl ether. The crude product (which contained thiol and disulfide) was dissolved in dimethylformamide containing dithiothreitol and triethyl amine. After 30 minutes the product was precipitated with excess ethyl ether and collected by filtration. This material was purified further by recrystallization from degassed acetonitrile containing dithiothreitol and a trace of triethyl amine to give pure N-[[(4-methyl-coumarin-7yl)amino]acetyl]cysteine hydrazide.

To 12 mg of LL-E33288$\gamma_1^I$ in 12 ml acetonitrile at 0° C. was added 4 mg of N-[[(4-methylcoumarin-7-yl)amino]acetyl]cysteine hydroxide in 1.2 ml dimethylformamide. After stirring overnight another 2 mg of N-[[(4-methyl-coumarin-7-yl)amino]acetyl]cysteine hydrazide in 0.6 ml dimethylformamide was added. The reaction was stirred for 3 days at 0° C. and filtered. The acetonitrile was evaporated and the resultant dimethylformamide solution was diluted with an excess of 1:1 hexanes/ether. The product was isolated by filtration and further purified by chromatography on silica gel with a 15–10% gradient of methanol in chloroform to yield 3 mg of the desired product. Retention time on reverse phase $C_{18}$ HPLC: 3.5 minutes using 45% acetonitrile/0.1 M aqueous ammonium acetate (LL-E33288$\delta_1^I$:15.5 min. in the same system).

EXAMPLE 6

3-Mercaptopropionyl hydrazide disulfide of LL-E33288$\alpha_3^I$

To 10 mg of LL-E33288$\alpha_3^I$ in 9 ml of acetonitrile at $-15°$ C. was added 6.6 mg of 3-mercaptopropionyl hydrazide in 1 ml acetonitrile. One equivalent of triethylamine or one equivalent of triethylamine and one equivalent of acetic acid were added. The reaction was allowed to stir at 0° C. for one hour and the solvent was then evaporated. The residue was chromatographed on silica gel with a 10–15% methanol-in-chloroform gradient to give the desired product. FABMS. m/g-1251 (M+H); retention time on reverse phase $C_{18}$ HPLC: 2.1 minutes in the system 45% acetonitrile/0.1 M aqueous ammonium acetate (LL-E33288$\alpha_5^I$:5.7 min. in the same system).

EXAMPLE 7

3-Mercaptopropionyl hydrazide disulfide of N-acetyl LL-E33288$\gamma_1^I$

To 10 mg of N-acetyl LL-E33288$\gamma_1^I$ in 10 ml of acetonitrile at −15° C. was added 1.5 eq of 3-mercaptopropionyl hydrazide in 85 μl acetonitrile. One equivalent of triethylamine was added. The reaction was allowed to stir at 0° C. for two hours and the solvent was then evaporated. The residue was chromatographed on silica gel with a 10–15% methanol-in-chloroform gradient to yield the desired product. FABMS, m/s=1450 (M+H); retention time on $C_{18}$ reverse phase HPLC:2.5 min. with 50% acetonitrile/0.05 M aqueous ammonium dihydrogen phosphate (N-acetyl LL-E33288$\gamma_1^I$:6.6 min. in the same system).

EXAMPLE 8

3-Mercaptopropionyl hydrazide disulfide of LL-E33288$\alpha_2^I$

To 10 mg of LL-E33288$\alpha_2^I$ in 10 ml of acetonitrile at −15° C. was added 1.5 eq of 3-mercaptopropionyl hydrazide in 1 ml acetonitrile. One equivalent of triethylamine was added. The reaction was allowed to stir at 0° C. for one hour and the solvent was then evaporated. The residue was chromatographed on silica gel with a 5–15% methanol-in-chloroform gradient to yield the desired product. FABMS, m/s=1248 (M+H); retention time on $C_{18}$ reverse phase HPLC:2.6 min. with 58% acetonitrile/0.05 M aqueous ammonium dihydrogen phosphate (LL-E33288$\alpha_2^I$:7.5 min. in the same system).

EXAMPLE 9

3-Mercaptopropionyl hydrazide disulfide of iodo LL-E33288 pseudoaglycone

To 10 mg of iodo LL-E33288 pseudoaglycone in 9 ml of acetonitrile at −15° C. was added 1.5 eq of 3-mercaptopropionyl hydrazide in 1 ml acetonitrile. One equivalent of triethylamine was added as a catalyst. The reaction was allowed to stir at 0° C. for one hour and the solvent was then evaporated. The residue was chromatographed on silica gel with a 10–15% methanol-in-chloroform gradient to yield the desired product. FABMS, m/s=1091 (M+H); retention time on $C_{18}$ reverse phase HPLC:2.8 min. with 50% acetonitrile/0.05 M aqueous ammonium dihydrogen phosphate (iodo LL-E33288 pseudoaglycone; 7.9 min. in the same system).

EXAMPLE 10

3-Mercaptobutyryl hydrazide disulfide of LL-E33288$\gamma_1^I$

To 17.2 g (0.2 moles) of crotonic acid was added 18 ml (0.26 moles) of thioacetic acid. This mixture was heated at reflux under argon for 6 hours. The excess thioacetic acid was removed under aspirator vacuum and the resultant oil was dissolved in 100 ml absolute ethanol containing 200 μl of concentrated sulfuric acid. This reaction was refluxed for 10 hours and then reduced in volume under aspirator vacuum. Hexanes were added and the resultant solution washed successively with two portions of saturated sodium bicarbonate and one portion of water. This solution was then dried with magnesium sulfate, filtered, and reduced in volume to an oil. This crude product was dissolved in 250 ml of methanol containing 12 ml of hydrazine and the resultant mixture was refluxed for 10 hours under argon. The reaction mixture was reduced in volume and then distilled rapidly by Kugelrohr and crystallized from a mixture of chloroform-hexanes to give 3-mercaptobutyryl hydrazide.

To 5 mg of LL-E33288$\gamma_1^I$ in 5 ml of acetonitrile at −15° C. was added 1.5 eq of 3-mercaptopropionyl hydrazide in 1 ml acetonitrile. One equivalent of triethylamine was added. The reaction was allowed to stir at 0° C. for one hour and the solvent was then evaporated. The residue was chromatographed on silica gel with a 10–15% methanol-in-chloroform gradient to yield the desired product. FABMS, m/e=1422 (M+H); retention time on $C_{18}$ reverse phase HPLC: 3.5 min. with 43% acetonitrile/0.05 M aqueous ammonium dihydrogen phosphate (LLO-E33288$\gamma_1^I$:13.4 min. in the same system).

EXAMPLE 11

3-Mercaptoisovaleryl hydrazide disulfide of LL-E33288$\gamma_1^I$

To 10 g (0.1 moles) of 3,3-dimethyl acrylic acid was added 9 ml (0.13 moles) of thioacetic acid. This mixture was heated at reflux under argon for 6 hours. The excess thioacetic acid was removed under aspirator vacuum and the resultant oil was dissolved in 100 ml absolute ethanol containing 200 μl of concentrated sulfuric acid. This reaction was refluxed for 34 hours before adding 16 ml of hydrazine. The resultant mixture was refluxed for 24 hours under argon. The reaction mixture was reduced in volume and then dissolved in a mixture of brine and saturated sodium bicarbonate. The product was extracted with several volumes of chloroform. The combined chloroform layers were dried with magnesium sulfate, filtered, and reduced in volume to an oil. This oil was purified by flash chromatography with a methanol-chloroform gradient and then crystallized from chloroform-hexanes to give 3-mercaptoisovaleryl hydrazide.

To 15 mg of LL-E33288$\gamma_1^I$ in 5 ml of acetonitrile at −15° C. was added 1.5 eq of 3-mercaptoisovaleryl hydrazide in 100 μl acetonitrile. One equivalent of triethylamine was added as a catalyst. The reaction was allowed to stir at ambient temperature for 3 hours and the solvent was then evaporated. The residue was chromatographed on silica gel with a 10–15% methanol-in-chloroform gradient to yield the desired product. FABMS, m/s=1436 (M+H); retention time on $C_{18}$ reverse phase HPLC:3.9 min. with 43% acetonitrile/0.05 M aqueous ammonium dihydrogen phosphate (LL-E33288$\gamma_1^I$:13.4 min. in the same system).

EXAMPLE 12 p-Mercaptodihydrocinnamyl hydrazide disulfide of LL-E33288$\gamma_1^I$

To 500 mg (2.75 mmol) of p-mercaptodihydrocinnamic acid was added 15 ml methanol containing one drop of concentrated sulfuric acid. The reaction was refluxed for 5 hours and then cooled to ambient temperature. Hydrazine (1.5 ml) was added and the resultant mixture was refluxed for 2 hours under argon and then stirred for 10 hours at ambient temperature. A 200 mg portion of dithiothreitol was added to reduce any disulfides present and the reaction mixture was cooled to −15°. The resultant crystals were filtered, washed with a mixture of ether and methanol, and then dried in a vacuum oven (50°/5 microns/10 hours) to give p-mercaptodihydrocinnamyl hydrazide.

To 25 mg of LL-E33288$\gamma_1^I$ in 25 ml of acetonitrile at −15° C. was added 1.5 eq of p-mercaptodihydrocinnamyl hydrazide in 1 ml acetonitrile. The residue was chromatographed on silica gel with a 10-15% methanol-in-chloroform gradient to yield the desired product. FABAMS, m/s=1484 (M+H); retention time on $C_{18}$ reverse phase HPLC:5.4 min. with 43% acetonitrile/0.05 M aqueous ammonium dihydrogen phosphate (LL-E33288$\gamma_1^I$:13.4 min. in the same system).

EXAMPLE 13

3-Mercaptoisovaleryl hydrazide disulfide of N-acetyl LL-E33288$\gamma_1^I$

To 20 mg of N-acetyl LL-E33288$\gamma_1^I$ in 15 ml of acetonitrile at −15° C. was added 3 eq of 3-mercaptoisovaleryl hydrazide in 6.2 ml acetonitrile. One equivalent of triethylamine was added. The reaction was allowed to stir at ambient temperature for 2 hours and the solvent was then exaporated. The residue was chromatographed on silica gel with a 10-15% methanol-in-chloroform gradient to yield the desired product. Retention time on $C_{18}$ reverse phase HPLC:2.5 min. with 50% acetonitrile/0.05 M aqueous ammonium dihydrogen phosphate (N-acetyl LL-E33288$\gamma_1^I$:6.6 min. in the same system).

EXAMPLE 14

3-Mercaptobutyryl hydrazide disulfide of N-acetyl LL-E33288$\gamma_1^I$

To 10 mg of N-acetyl LL-E33288$\gamma_1^I$ in 7.5 ml of acetonitrile at −15° C. was added 3 eq of 3-mercaptobutyryl hydrazide in 5 ml acetonitrile. One equivalent of triethylamine was added. The reaction was allowed to stir at ambient temperature for 10 hours and the solvent was then evaporated. The residue was chromatographed on silica gel with a 10-15% methanol-in-chloroform gradient to yield the desired product. Retention time on $C_{18}$ reverse phase HPLC:7.3 min. with 43% acetonitrile/0.05 M aqueous ammonium dihydrogen phosphate (N-acetyl LL-E33288$\gamma_1^I$:5.6 min. in the same system).

EXAMPLE 15 p-Mercaptodihydrocinnamyl hydrazide disulfide of N-acetyl LL-E33288$\gamma_1^I$

To 10 mg of N-acetyl LL-E33288$\gamma_1^I$ in 7.5 ml of acetonitrile at −15° C. was added 3.0 eq of p-mercaptodihydrocinnamyl hydrazide in 2.0 ml acetonitrile. One equivalent of triethylamine was added. The reaction was allowed to stir at ambient temperature for 2 hours and the solvent was then evaporated. The residue was chromatographed on silica gel with a 10-15% methanol-in-chloroform gradient to yield the desired product. Retention time on $C_{18}$ reverse phase HPLC:7.3 min. with 43% acetonitrile/0.05 M aqueous ammonium dihydrogen phosphate (N-acetyl LL-E33288$\gamma_1^I$:5.6 min. in the same system).

EXAMPLE 16

NON-SPECIFIC CONJUGATION TO PROTEINS

The hydroxysuccinimide ester described in Example 3 was covalently attached to antibodies under slightly alkaline conditions. The following is a general procedure used to make the antibody conjugates listed in Table 6. Antibody at a concentration of 3-5 mg/ml in phosphate buffer containing 0.1 M sodium chloride, pH 7.5 was reacted with a 5-20-fold molar excess of the product from Example 3 with stirring, at room temperature for from 1-4 hours. The conjugated protein was desalted chromatographically and aggregated protein was separated from monomeric material by gel filtration HPLC. Monomeric fractions were pooled and concentrated.

TABLE 6

Non-specific conjugates prepared using the product of Example 3

| MoAb | Drug Loading M/M |
| --- | --- |
| Lym 1 | 5.2 |
| B72.3 | 6.0 |
| B72.3 | 2.9 |

EXAMPLE 17

SITE-SPECIFIC CONJUGATE PREPARATION

The general method for attaching hydrazide derivatives of drugs to oxidized antibodies is described in T. J. McKearn, et a., in U.S. Pat. No. 4,671,958. The procedure has been applied to preparing antibody conjugates from the products of Examples 4 to 15 with specific modifications as described below. The products from these reactions and their characteristics are summarized in Table 7.

(A) Antibody Oxidation Antibody at a concentration of 5 to 10 mg/ml was dialyzed overnight against a 200 fold volume of 50 mM sodium acetate buffer, pH 5.5 containing 0.1 M sodium chloride (Buffer A). After dialysis, the MoAb was oxidized with 15 mM to 200 mM periodic acid in 0.2 M sodium acetate. The oxidation was allowed to proceed in the dark, with stirring, at 4° C. for 45 minutes after which time the oxidized MoAb was desalted on a ≧5 bed volume Sephadex G-25 column. The degree of oxidation of the antibody was assessed by reaction with p-nitrophenylhydrazine and comparing absorbance of the protein at 280 mm vs. p-nitrophenylhydrazine at 395 mm.

(B) Drug Hydrazide Conjugation The oxidized MoAb was reacted with 10 to 200-fold molar excess of drug hydrazide. The hydrazides were dissolved into dimethylformamide and added to the aqueous solution of MoAb. To avoid precipitation of MoAb, the final volume of dimethylformamide added did not exceed 10% of the total reaction volume. Reaction was allowed to proceed for 3 hours at room temperature, with stirring. To prevent crosslinking of unreacted aldehydes and subsequent aggregation, a blocking agent, acetyl hydrazide was added in 100-fold molar excess three hours after addition of the drug hydrazide. To stabilize the Schiff's base linkage between aldehyde and drug hydrazide (a hydrazone), the product generally was reduced to an alkyl hydrazine by the addition of 10 mM sodium cyanoborohydride, allowing the reaction to proceed for one more hour (total conjugation time—4 hours). The conjugate was chromatographically desalted and exhaustively dialyzed (minimum time 48 hours) into pH 6.5 phosphate buffer for storage and testing.

Conjugates were analyzed for the presence of aggregates by gel filtration HPLC and for free drug by reverse phase HPLC. Drug loading was determined spectroscopically using the extinction coefficients of both the antibody and the drug to estimate molar concentrations of drug in conjugates.

TABLE 7

| MoAb | Preparation | Drug Loading M/M |
|---|---|---|
| Hydrazide conjugates prepared from the product of Example 4 | | |
| Lym 1 | #1 | 1.4 |
| | #2 | 2.4 |
| | #3 | 1.0 |
| | #4 | 6.7 |
| | #5 | 3.3 |
| Lym 2 | #1 | 2.9 |
| | #2 | 1.9 |
| | #3 | 2.0 |
| | #4 | 2.8 |
| B72.3 | #1 | 2.3 |
| | #2 | 1.3 |
| | #3 | 2.5 |
| CTM-01 | #1 | 3.1 |
| | #2 | 2.3 |
| | #3 | 2.9 |
| MAC-68 | #1 | 1.7 |
| | #2 | 3.1 |
| | #3 | 2.4 |
| Hydrazide Conjugates prepared from the product of Example 5 | | |
| Lym 1 | #1 | 0.15 |
| | #2 | 0.76 |
| | #3 | 3.2 |
| Hydrazide conjugates prepared from the product of Example 6 | | |
| Lym 1 | | 3.0 |
| CT-M-01 | #1 | 2.4 |
| | #2 | 2.9 |
| Hydrazide conjugates prepared from the product of Example 7 | | |
| Lym 1 | | 2.8 |
| Lym 2 | | 1.4 |
| B72.3 | #1 | 2.1 |
| | #2 | 2.4 |
| CT-M-01 | #1 | 1.6 |
| | #2 | 3.6 |
| | #3 | 2.5 |
| | #4 | 2.4 |
| Hydrazide conjugates prepared from the product of Example 8 | | |
| CT-M-01 | | 4.8 |
| Hydrazide conjugates prepared from the product of Example 9 | | |
| CT-M-01 | | 3.0 |
| Hydrazide conjugates prepared from the product of Example 10 | | |
| Lym 1 | | 3.7 |
| Hydrazide conjugates prepared from the product of Example 11 | | |
| Lym 1 | | 6.2 |
| Hydrazide conjugates prepared from the product of Example 12 | | |
| Lym 1 | | 3.5 |

We claim:

1. A carrier-drug conjugate of the formula

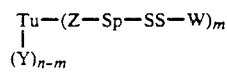

prepared from a compound of formula $CH_3SSS$-W wherein $CH_3SSS$-W is an antitumor antibiotic designated as LL-E33288$\alpha_1^{Br}$, $\alpha_1^I$, $\alpha_2^{Br}$, $\alpha_3^{Br}$, $\alpha_3^I$, $\alpha_4^{Br}$, $\beta_1^{Br}$, $B_1^I$, $\beta_2^{Br}$, $\beta_2^I$, $\gamma_1^{Br}$, $\gamma_1^I$, $\delta_1^I$, the iodo or bromo pseudoaglycones, their dihydro or N-acyl counterparts, BBM-1675, FR-900405, FR-900406, PD 114759, PD 115028, CL-1577A, CL-1577B, CL-1577D, CL-1577E, CL-1724 or their N-acetyl counterparts comprising:

reacting $CH_3SSS$-W with a compound of general formula A-Sp-SH, wherein Sp is a straight or branched-chain divalent or trivalent ($C_1$–$C_{18}$) radical, divalent or trivalent aryl or heteroaryl radical, divalent or trivalent ($C_3$–$C_{18}$) cycloalkyl or heterocycloalkyl radical, divalent or trivalent aryl- or heteroaryl-alkyl ($C_1$–$C_{18}$) radical, divalent or trivalent cycloalkyl- or heterocycloalkyl-alkyl ($C_1$–$C_{18}$) radical or divalent or trivalent ($C_2$–$C_{18}$) unsaturated alkyl radical, wherein if Sp is a trivalent radical, it can be additionally substituted by amino, alkylamino, arylamino, heteroarylamino, carboxyl, lower alkoxy, hydroxy, thiol, or lower alkylthio groups; and Q is, or can be subsequently converted to, halogen, amino, alkylamino, carboxyl, carboxaldehyde, hydroxy, tiol, α-haloacetyloxy, lower alkyldicarboxyl, —CONHNH$_2$, —NHCONHNH$_2$, —NHCSNHNH$_2$, —ONH$_2$, —CON$_3$,

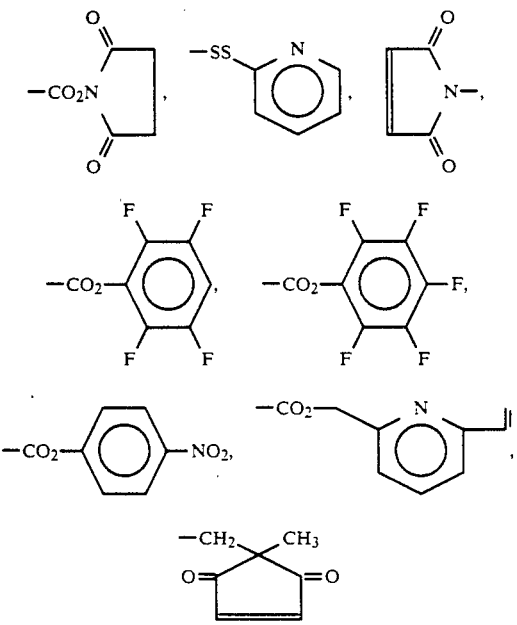

to produce an intermediate of formula Q-Sp-SS-W, wherein Q, Sp, and W are as hereinbefore defined, reacting Q-Sp-SS-W with a molecule of the formula Tu-(Y)$_n$ wherein the carrier Tu is defined as a mono- or polyclonal antibody, its fragments, its chemically or genetically manipulated counterparts, or growth factors or steroids; Y is a side-chain amino, carboxy, or thiol group of a protein, an aldehyde derived from glycoprotein carbohydrate residues, or an amidoalkylathio group; and n is an integer of from 1 to 100, to produce a compound of the formula:

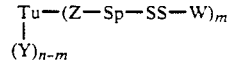

wherein Tu, Y, Sp, W, and n are as hereinbefore defined, and Z is formed from covalent reaction of the groups Q and Y directly or after subsequent reduction, and Z is —CONH—, —CONHN=CH—, —CONHNHCH$_2$—, —NHCONHN=CH—, —NHCONHNHCH$_2$, —NHCSNHN=CH—, —NHCSNHNHCH$_2$—, —OH=CH—, —NH—, —NHCH$_2$—, —N=CH—, —CO$_2$—, —NHCH$_2$CO$_2$—, —SS—,

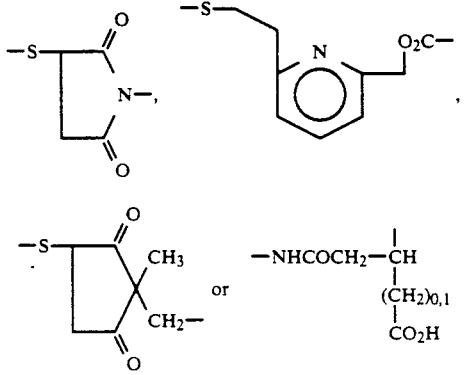

and m is 0.1 to 15.

2. A protein-drug conjugate according to claim 1 of the formula

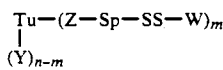

prepared from the class of antitumor antibiotics designated LL-E33288 (CH$_3$SSS-W) comprising: p1 displacing the dithiomethyl moiety with a compound of formula Q-Sp-SH, wherein Sp is straight or branched-chain divalent or trivalent (C$_2$–C$_{10}$) radicals or divalent or trivalent aryl- or heteroaryl-alkyl (C$_2$–C$_5$) radicals, wherein if Sp is a trivalent radical, it can be additionally substituted by amino, heteroarylamino, hydroxy, or thiol groups; and Q is, or can be subsequently converted to, carboxyl, lower alkyldicarboxylanhydride, —CONHNH$_2$, or

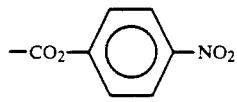

to produce an intermediate of general formula A-Sp-SS-W, wherein Q, Sp, and W are as hereinbefore defined, reacting Q-Sp-SS-W with a molecule of the formula Tu-(Y)$_n$ wherein Tu is a monoclonal antibody which exhibits preferential reactivity with a human tumor-associated antigen, Y is a side-chain amino group on the antibody, or an aldehyde generated by oxidation of the carbohydrate groups of the antibody, and n is an integer of from 1 to 100, to produce a compound of the formula:

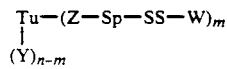

wherein Tu, Y, Sp, W, and n are as hereinbefore defined, and Z is formed from covalent reaction of the groups Q and Y directly or after subsequent reduction, and Z is —CONH—, —CONHN=CH—, —CONHNHCH$_2$—, or

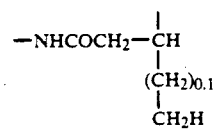

and m is 0.1 to 15.

3. A protein-drug conjugate according to claim 2 wherein CH$_3$SSS-W is the antitumor antibiotic designated LL-E33288δ$_1^I$ having:
a) ultraviolet spectrum as shown in FIG. I;
b) a proton magnetic resonance spectrum as shown in FIG. II; and
c) an infrared spectrum as shown in FIG. III.

4. A protein-drug conjugate according to claim 2 wherein CH$_3$SSS-W is the antitumor antibiotic designated LL-E33288α$_2^I$ having:
a) a proton magnetic resonance spectrum as shown in FIG. IV; and
b) a carbon-13 nuclear magnetic resonance spectrum as shown in FIG. V.

5. A protein-drug conjugate according to claim 2 wherein CH$_3$SSS-W is the antitumor antibiotic designated LL-E33288α$_3^I$ having:
a) ultraviolet spectrum as shown in FIG. VI;
b) an infrared spectrum as shown in FIG. VII;
c) a proton magnetic resonance spectrum as shown in FIG. VIII; and
d) a carbon-13 nuclear magnetic resonance spectrum as shown in FIG. IX.

6. A protein-drug conjugate according to claim 2 wherein CH$_3$SSS-W is the antitumor antibiotic designated N-acetyl LL-E33288δ$_1^I$ having:
a) ultraviolet spectrum as shown in FIG. X;
b) an infrared spectrum as shown in FIG. XI;
c) a proton magnetic resonance spectrum as shown in FIG. XII; and
d) a carbon-13 nuclear magnetic resonance spectrum as shown in FIG. XIII.

7. A protein-drug conjugate according to claim 2 wherein CH$_3$SSS-W is the antitumor antibiotic designated iodo LL-E33288 pseudoaglycone having:
a) ultraviolet spectrum as shown in FIG. XIV;
b) an infrared spectrum as shown in FIG. XV;
c) a proton magnetic resonance spectrum as shown in FIG. XVI; and
d) a carbon-13 nuclear magnetic resonance spectrum as shown in FIG. XVII.

8. A protein-drug conjugate according to claim 2 wherein Tu is the monoclonal antibody designated Lym 1.

9. A protein-drug conjugate according to claim 2 wherein Tu is the monoclonal antibody designated Lym 2.

10. A protein-drug conjugate according to claim 2 wherein Tu is the monoclonal antibody designated CT-M-01.

11. A protein-drug conjugate according to claim 2 wherein Tu is the monoclonal antibody designated B72.3.

12. A protein-drug conjugate according to claim 2 wherein Tu is the monoclonal antibody designated MAC-68.

13. A protein-drug conjugate according to claim 2 wherein Q is the hydroxysuccinimide ester of a carboxyl group, Sp is —CH$_2$CH$_2$—, Y is —NH$_2$, Z is —CONH—, and m is 0.5 to 15.

14. A protein-drug conjugate according to claim 2 wherein Q is the hydroxysuccinimide ester of a carboxyl group, Sp is —CH$_2$CH(CH$_3$)—, Y is —NH$_2$, Z is —CONH—, and m is 0.5 to 15.

15. A protein-drug conjugate according to claim 2 wherein Q is the 4-nitrophenyl ester of a carboxyl group, Sp is —CH$_2$CH$_2$—, Y is —NH$_2$, Z is —CONH—, and m is 0.5 to 15.

16. A protein-drug conjugate according to claim 2 wherein Q is the hydroxysuccinimide ester of a carboxyl group, Sp is —CH$_2$C(CH$_3$)$_2$—, Y is —NH$_2$, Z is —CONH—, and m is 0.5 to 15.

17. A protein-drug conjugate according to claim 2 wherein Q is the hydroxysuccinimide ester of a carboxyl group, Sp is

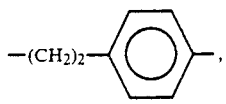

Y is —NH$_2$, Z is —CONH—, and m is 0.5 to 15.

18. A protein-drug conjugate according to claim 2 wherein Q is —CONHNH$_2$, Sp is —CH$_2$CH$_2$—, Y is —CHO, Z is —CONHN=CH—, and m is 0.1 to 10.

19. A protein-drug conjugate according to claim 2 wherein Q is —CONHNH$_2$, Sp is —CH$_2$CH$_2$—, Y is —CHO, Z is —CONHNHCH$_2$—, and m is 0.1 to 10.

20. A protein-drug conjugate according to claim 2 wherein Q is —CONHNH$_2$, Sp is —CH$_2$CH(CH$_3$)—, Y is —CHO, Z is —CONHN=CH—, and m is 0.1 to 10.

21. A protein-drug conjugate according to claim 2 wherein Q is —CONHNH$_2$, Sp is —CH$_2$CH(CH$_3$)—, Y is —CHO, Z is —CONHNHCH$_2$—, and m is 0.1 to 10.

22. A protein-drug conjugate according to claim 2 wherein Q is —CONHNH$_2$, Sp is —CH$_2$C(CH$_3$)$_2$—, Y is —CHO, Z is —CONHN=CH—, and m is 0.1 to 10.

23. A protein-drug conjugate according to claim 2 wherein Q is —CONHNH$_2$, Sp is —CH$_2$C(CH$_3$)$_2$—, Y is —CHO, Z is —CONHNHCH$_2$—, and m is 0.1 to 10.

24. A protein-drug conjugate according to claim 2 wherein Q is —CONHNH$_2$, Sp is

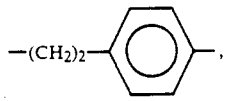

Y is —CHO, Z is —CONHN=CH—, and m is 0.1 to 10.

25. A protein-drug conjugate according to claim 2 wherein Q is —CONHNH$_2$, Sp is

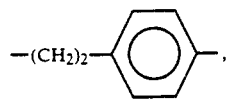

Y is —CHO, Z is —CONHNHCH$_2$—, and m is 0.1 to 10.

26. A protein-drug conjugate according to claim 2 wherein Q is —CONHNH$_2$, Sp is

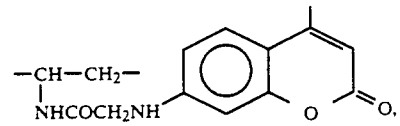

Y is —CHO, Z is —CONHN=CH—, and m is 0.1 to 10.

27. A protein-drug conjugate according to claim 2 wherein Q is —CONHNH$_2$, Sp is

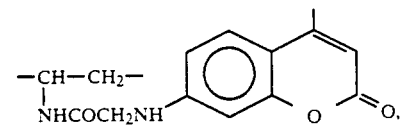

Y is —CHO, Z is —CONHNHCH$_2$—, and m is 0.1 to 10.

28. A protein-drug conjugate according to claim 8 wherein CH$_3$SSS-W is LL-E33288δ$_1^I$, Q is —CONHNH$_2$, Sp is —CH$_2$CH$_2$—, Y is —CHO, Z is —CONHNHCH$_2$—, and m is 0.1 to 10.

29. A protein-drug conjugate according to claim 10 wherein CH$_3$SSS-W is LL-E33288α$_3^I$, Q is —CONHNH$_2$, Sp is —CH$_2$CH$_2$—, Y is —CHO, Z is —CONHNHCH$_2$—, and m is 0.1 to 10.

30. A protein-drug conjugate according to claim 10 wherein CH$_3$SSS-W is N-acetyl LL-E33288δ$_1^I$, Q is —CONHNH$_2$, Sp is —CH$_2$CH$_2$—, Y is —CHO, Z is —CONHNHCH$_2$—, and m is 0.1 to 10.

31. A protein-drug conjugate according to claim 8 wherein CH$_3$SSS-W is LL-E33288δ$_1^I$, Q is —CONHNH$_2$, Sp is —CH$_2$CH(CH$_3$)—, Y is —CHO, Z is —CONHNHCH$_2$—, and m is 0.1 to 10.

32. A protein-drug conjugate according to claim 10 wherein CH$_3$SSS-W is LL-E33288α$_3^I$, Q is —CONHNH$_2$, Sp is —CH$_2$C(CH$_3$)$_2$—, Y is —CHO—, Z is —CONHNHCH$_2$—, and m is 0.1 to 10.

33. A protein-drug conjugate according to claim 10 wherein CH$_3$SSS-W is N-acetyl LL-E33288δ$_1^I$, Q is —CONHNH$_2$, Sp is

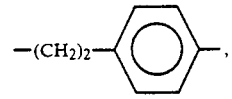

Y is —CHO, Z is —CONHNHCH$_2$—, and m is 0.1 to 10.

* * * * *